US006371994B2

(12) United States Patent
Lang et al.

(10) Patent No.: US 6,371,994 B2
(45) **Date of Patent: *Apr. 16, 2002**

(54) DYE COMPOSITION FOR KERATIN FIBERS, WITH A CATIONIC DIRECT DYE AND A POLYOL OR POLYOL ETHER

(75) Inventors: Gérard Lang, Saint Prix; Jean Cotteret, Verneuil sur Seine, both of (FR)

(73) Assignee: L'Oreal S.A., Paris (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/321,889

(22) Filed: May 28, 1999

(30) Foreign Application Priority Data

May 28, 1998 (FR) .......................................... 98 06752

(51) Int. Cl.[7] ................................................ A61K 7/13

(52) U.S. Cl. ...................... 8/426; 8/408; 8/429; 8/431; 8/609; 8/610; 8/611; 8/613; 8/654; 8/655; 8/657; 8/659

(58) Field of Search .......................... 8/426, 406, 407, 8/405, 408, 429, 431, 609, 610, 611, 613, 654, 655, 657, 659

(56) References Cited

U.S. PATENT DOCUMENTS

| | | | | |
|---|---|---|---|---|
| 2,983,651 A | * 5/1961 | Seemuller | 8/426 |
| 3,482,923 A | * 12/1969 | Boosen et al. | 8/426 |
| 3,578,386 A | * 5/1971 | Kalopissis et al. | 8/426 |
| 3,632,290 A | * 1/1972 | Tucker et al. | 8/426 |
| 3,869,454 A | * 3/1975 | Lang et al. | 8/426 |
| 3,955,918 A | * 5/1976 | Lang | 8/426 |
| 3,985,499 A | 10/1976 | Lang et al. | 8/426 |
| 4,025,301 A | * 5/1977 | Lang | 8/426 |
| 4,151,162 A | 4/1979 | Lang et al. | 534/607 |
| 5,474,578 A | * 12/1995 | Chan et al. | 8/426 |
| 5,708,151 A | * 1/1998 | Mockli | 534/608 |
| 5,879,412 A | * 3/1999 | Rondeau et al. | 8/426 |
| 5,919,273 A | * 7/1999 | Rondeau et al. | 8/426 |
| 5,993,490 A | * 11/1999 | Rondeau et al. | 8/426 |
| 6,001,135 A | * 12/1999 | Rondeau et al. | 8/426 |

FOREIGN PATENT DOCUMENTS

| | | |
|---|---|---|
| DE | 3 829 870 | 4/1989 |
| EP | 0 714 954 | 6/1996 |
| EP | 0 850 636 | 7/1998 |
| EP | 0 850 637 | 7/1998 |
| EP | 0 850 638 | 7/1998 |
| FR | 2 140 205 | 1/1973 |
| FR | 2 189 006 | 1/1974 |
| FR | 2 282 860 | 3/1976 |
| FR | 2 285 851 | 4/1976 |
| FR | 2 586 913 | 3/1987 |
| WO | WO 95/01772 | 1/1995 |
| WO | WO 95/15144 | 6/1995 |

OTHER PUBLICATIONS

English language Derwent Abstract of DE 3 829 870, Apr. 1989.
English language Derwent Abstract of EP 0 714 954, Jun. 1996.
English language Derwent Abstract of EP 0 850 636, Jul. 1998.
English language Derwent Abstract of Ep 0 850 637, Jul. 1998.
English language Derwent Abstract of EP 0 850 638, Jul. 1998.
English language Derwent Abstract of FR 2 189 006, Jan. 1974.
English language Derwent Abstract of FR 2 285 851, Apr. 1976.
English language Derwent Abstract of FR 2 140 205, Jan. 1973.
English language Derwent Abstract of FR 2 586 913, Mar. 1987.

* cited by examiner

*Primary Examiner*—Margaret Einsmann
(74) *Attorney, Agent, or Firm*—Finnegan, Henderson, Farabow, Garrett & Dunner, L.L.P.

(57) ABSTRACT

The invention relates to a dye composition for keratin fibers, in particular for human keratin fibers such as the hair, comprising at least one cationic direct dye of given formula and at least glycerol and/or one specific polyol and/or polyol ether. The invention also relates to the dyeing processes and devices using this composition.

36 Claims, No Drawings

DYE COMPOSITION FOR KERATIN FIBERS, WITH A CATIONIC DIRECT DYE AND A POLYOL OR POLYOL ETHER

The invention relates to a dye composition for keratin fibers, in particular for human keratin fibers such as the hair, comprising, in a medium which is suitable for dyeing, at least one cationic direct dye of given formula, and at least glycerol and/or one specific polyol and/or polyol ether.

The invention also relates to the dyeing processes and devices using the composition.

Two types of coloration can be distinguished in the field of hair treatment.

The first is semi-permanent or temporary dyeing, or direct dyeing, which involves dyes capable of giving the hair's natural color a more or less pronounced color change which may withstand shampooing several times. These dyes are known as direct dyes; they can be used with or without an oxidizing agent. In the presence of an oxidizing agent, the aim is to obtain a lightening coloration. The lightening coloration is carried out by applying to the hair the mixture, prepared at the time of use, of a direct dye and an oxidizing agent, and in particular makes it possible to obtain, by lightening the melanin in the hair, an advantageous effect such as a unified color in the case of grey hair, or to bring out the color in the case of naturally pigmented hair.

The second is permanent dyeing or oxidation dyeing. This is carried out with dyes known as "oxidation" dyes comprising oxidation dye precursors and couplers.

Oxidation dye precursors, commonly known as "oxidation bases", are initially colorless or weakly colored compounds which develop their dyeing power on the hair in the presence of oxidizing agents added at the time of use, leading to the formation of colored compounds and dyes. The formation of these colored compounds and dyes results either from an oxidative condensation of the "oxidation bases" with themselves or from an oxidative condensation of the "oxidation bases" with coloration modifier compounds commonly known as "couplers", which are generally present in the dye compositions used in oxidation dyeing.

In order to vary the shades obtained with the said oxidation dyes, or to enrich them with glints, it is known to add direct dyes thereto.

Among the cationic direct dyes available in the field of dyeing keratin fibers, in particular human keratin fibers, compounds which are already known are those whose structure is developed in the text which follows; nevertheless, these dyes lead to colorations which have properties that are still insufficient, e.g., the homogeneity of the color distributed along the fiber ("unison"), in which case it is said that the coloration is too selective, the staying power, in terms of resistance to the various attacking factors to which the hair may be subjected (light, bad weather, shampooing) and the intensity.

After considerable research conducted in this matter, the inventors have now discovered that it is possible to obtain novel compositions for dyeing keratin fibers, which are capable of leading to colorations which can be more resistant to the various attacking factors to which the hair may be subjected, and can be more intense and less selective, by combining at least glycerol and/or one specific polyol and/or polyol ether with at least one cationic direct dye known in the prior art, and of formula (I) defined below.

This discovery forms the basis of the present invention.

A first subject of the present invention is thus a composition for dyeing keratin fibers, and in particular human keratin fibers such as the hair, containing, in a medium which is suitable for dyeing, (i) at least one cationic direct dye whose structure corresponds to formula (I) below, characterized in that it also contains (ii) at least glycerol and/or one specific polyol and/or polyol ether.

(i) The cationic direct dye which can be used according to the present invention is a compound of formula (I) below:

(I)

A—N=N—B in which:

the symbol A represents a group chosen from structures $A_1$ to $A_3$ below:

$A_1$

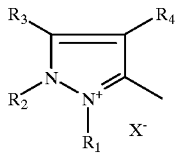

$A_2$

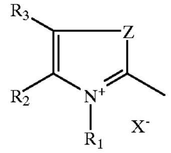

$A_3$

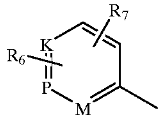

in which structures $A_1$ to $A_3$, $R_1$ is chosen from $C_{1-C_4}$ alkyl radicals and a phenyl radical having a substituent chosen from $C_1$–$C_4$ alkyl radicals and halogen atoms chosen from chlorine, bromine, iodine and fluorine;

$R_2$ is chosen from $C_1$–$C_4$ alkyl radicals and a phenyl radical;

$R_3$ and $R_4$, which may be identical or different, are chosen from $C_1$–$C_4$ alkyl radicals and a phenyl radical or, in the case of structure $A_1$, can together form a substituted benzene ring, and in the case of structure $A_2$, can together form a benzene ring optionally having at least one substituent chosen from $C_1$–$C_4$ alkyl, $C_1$–$C_4$ alkoxy and $NO_2$ radicals;

$R_3$ can also denote a hydrogen atom;

Z is chosen from an oxygen atom, a sulphur atom, and —$NR_2$ groups;

M is chosen from —CH, —CR, where R is chosen from $C_1$–$C_4$ alkyl radicals, and —$N^+R_5(X^-)_r$ groups;

K is chosen from —CH, —CR, where R is chosen from $C_1$–$C_4$ alkyl radicals, and —$N^+R_5(X^-)_r$ groups;

P is chosen from —CH, —CR, where R is chosen from $C_1$–$C_4$ alkyl radicals, and —$N^+R_5(X^-)_r$ r denotes 0 or 1;

$R_5$ is chosen from an atom $O^-$, $C_1$–$C_4$ alkoxy radicals and $C_1$–$C_4$ alkyl radicals;

$R_6$ and $R_7$, which may be identical or different, are chosen from a hydrogen atom, halogen atoms chosen from chlorine, bromine, iodine and fluorine, $C_1$–$C_4$ alkyl radicals, $C_1$–$C_4$ alkoxy radicals and an —$NO_2$ radical;

$X^{31}$ is an anion, preferably chosen from chloride, iodide, methyl sulphate, ethyl sulphate, acetate and perchlorate;

with the proviso that, if $R_4$ is a $C_1$–$C_4$ alkyl radical and Z is a sulphur atom, $R_3$ is not a hydrogen atom;

if $R_5$ is $O^-$, then r is zero;

if K or P or M is —$N^+$—$C_1$–$C_4$ -alkyl $X^-$, then $R_6$ or $R_7$ is other than a hydrogen atom;

if K is —$N^+R_5(X^-)_r$, then M=P and is —CH or —CR;

if M is —$N^+R_5(X^-)_r$, then K=P and is —CH or —CR;

if P is —$N^+R_5(X^-)_r$, then K=M and is —CH or —CR;

if Z is —$NR_2$ and $R_2$ is a $C_1$–$C_4$ alkyl radical, then at least one of the radicals $R_1$, $R_3$ or $R_4$ of structure $A_2$ is other than a $C_1$–$C_4$ alkyl radical;

the symbol B represents:

(a) a group of structure $B_1$ below:

$B_1$

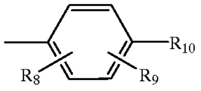

in which structure $B_1$, $R_8$ is chosen from a hydrogen atom, halogen atoms chosen from chlorine, bromine, iodine and fluorine, $C_1$–$C_4$ alkyl radicals, $C_1$–$C_4$ alkoxy radicals, a radical —OH, a radical —$NO_2$, —$NHR_{11}$ radicals, —$NR_{12}R_{13}$ radicals, and —$NHCO(C_1$–$C_4)$ alkyl radicals or forms, with $R_9$, a 5- or 6-membered ring which may contain at least one hetero atom chosen from nitrogen, oxygen and sulphur;

$R_9$ is chosen from a hydrogen atom, halogen atoms chosen from chlorine, bromine, iodine and fluorine, $C_1$–$C_4$ alkyl radicals, and $C_1$–$C_4$ alkoxy radicals, or forms, with $R_{10}$ or $R_{11}$, a 5- or 6-membered ring which may contain at least one hetero atom chosen from nitrogen, oxygen and sulphur;

$R_{10}$ is chosen from a hydrogen atom, an —OH radical, —$NHR_{11}$ radicals and —$NR_{12}R_{13}$ radicals;

$R_{11}$ is chosen from a hydrogen atom, $C_1$–$C_4$ alkyl radicals, $C_1$–$C_4$ monohydroxyalkyl radicals, $C_2$–$C_4$ polyhydroxyalkyl radicals and a phenyl radical;

$R_{12}$ and $R_{13}$, which may be identical or different, are chosen from $C_1$–$C_4$ alkyl radicals, $C_1$–$C_4$ monohydroxyalkyl radicals and $C_2$–$C_4$ polyhydroxyalkyl radicals; or (b) a 5- or 6-membered nitrogenous heterocyclic group which can contain at least one other hetero atom and/or at least one carbonyl group and which can have at least one substituent chosen from $C_1$–$C_4$ alkyl, amino and phenyl radicals, and in particular a group of structure B2 below:

$B_2$

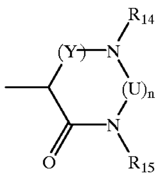

in which structure B2, $R_{14}$ and $R_{15}$, which may be identical or different, are chosen from a hydrogen atom and $C_1$–$C_4$ alkyl and phenyl radicals;

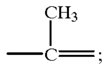

Y denotes a —CO— radical or a radical n=0 or 1, where, when n denotes 1, U denotes a —CO— radical.

In the structures defined above, the $C_1$–$C_4$ alkyl or alkoxy group preferably denotes methyl, ethyl, butyl, methoxy or ethoxy.

The cationic direct dyes of formula (I) which can be used in the dye compositions in accordance with the invention are known compounds and are described, for example, in patent applications FR-2,189,006, FR-2,285,851 and FR-2,140,205 and its Certificates of Addition, the disclosures of all of which are specifically incorporated by reference herein.

Among the cationic direct dyes of formula (I) which can be used in the dye compositions in accordance with the invention, those of formula (I) in which the symbol A denotes structure A3 while the symbol B denotes structure B1 or B2 are particularly preferred.

Among these compounds, mention may especially be made more particularly of the compounds of structures $(I)_1$ to $(I)_{77}$ below:

$(I)_1$

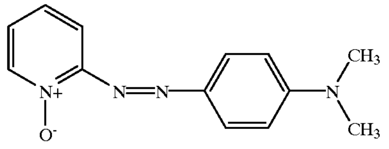

$(I)_2$

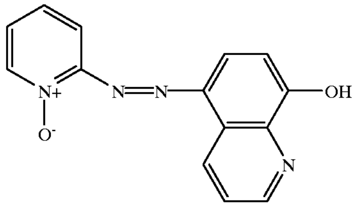

$(I)_3$

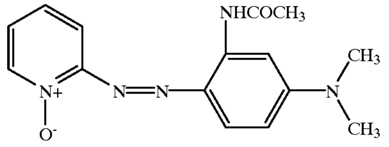

$(I)_4$

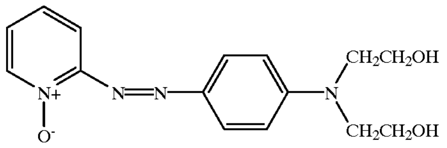

$(I)_5$

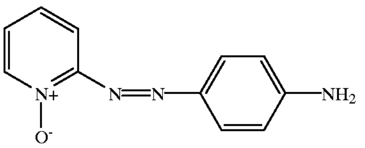

-continued
(I)6
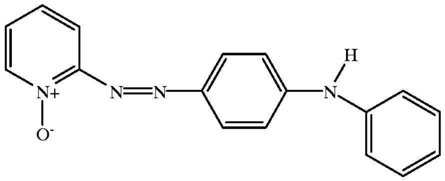
(I)7
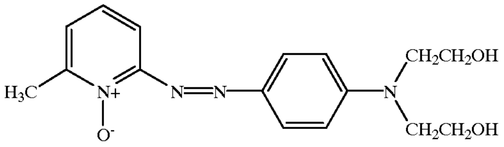
(I)8
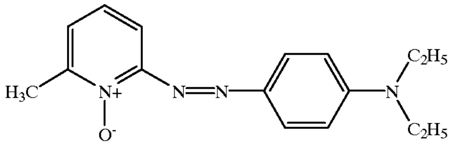
(I)9
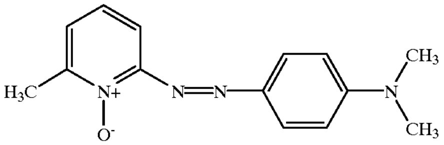
(I)10
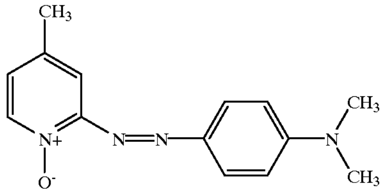
(I)11
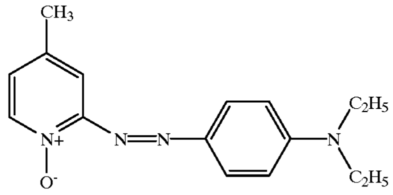
(I)12
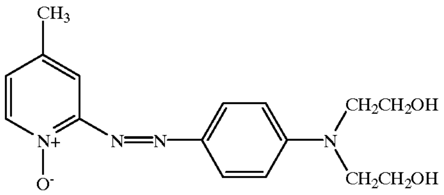
(I)13
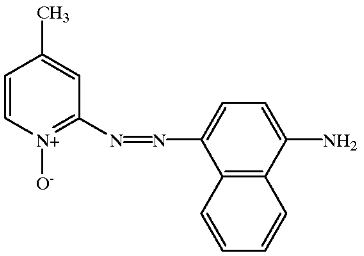
-continued
(I)14
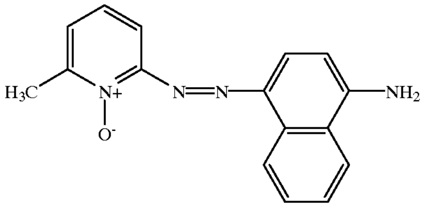
(I)15
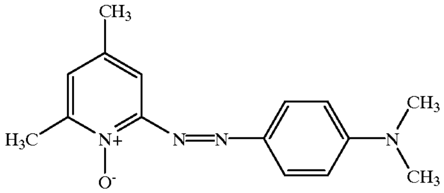
(I)16
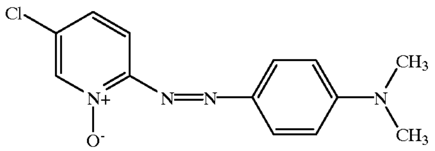
(I)17
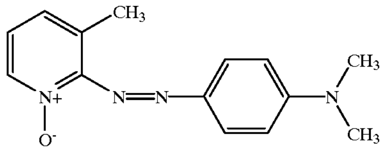
(I)18
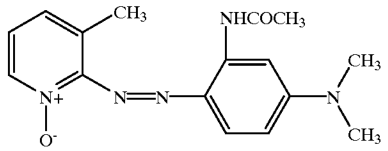
(I)19
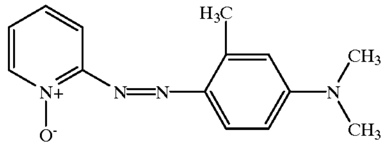
(I)20
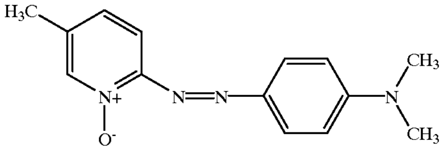
(I)21
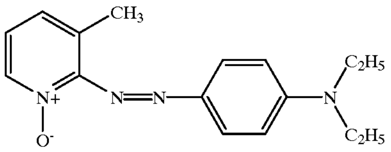

-continued
$(I)_{22}$
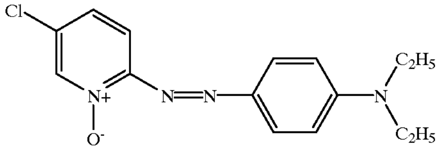
$(I)_{23}$
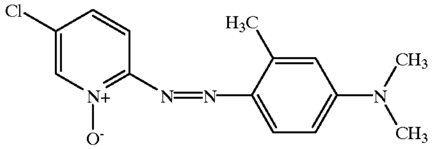
$(I)_{24}$
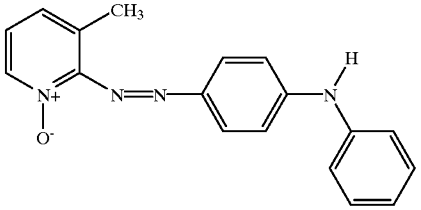
$(I)_{25}$
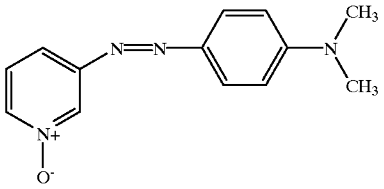
$(I)_{26}$
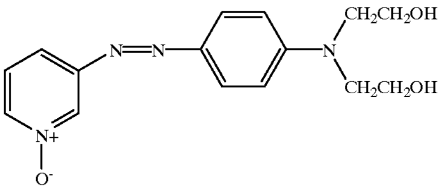
$(I)_{27}$
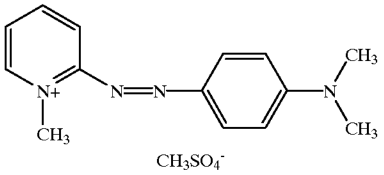
$(I)_{28}$
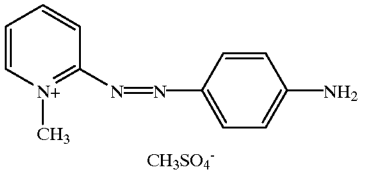
$(I)_{29}$
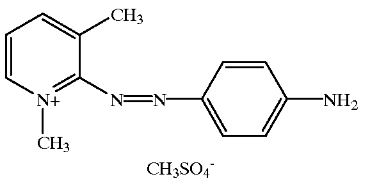
-continued
$(I)_{30}$
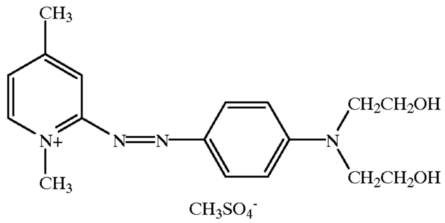
$(I)_{31}$
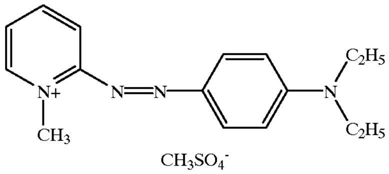
$(I)_{32}$
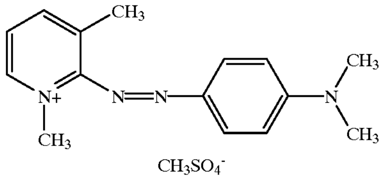
$(I)_{33}$
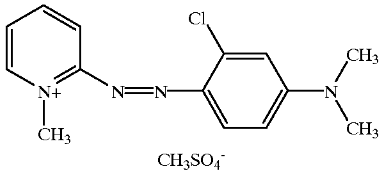
$(I)_{34}$
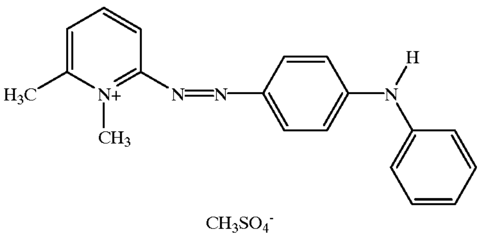
$(I)_{35}$
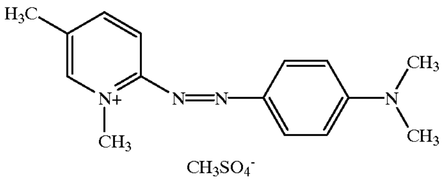
$(I)_{36}$
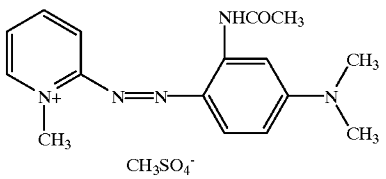

-continued
(I)37
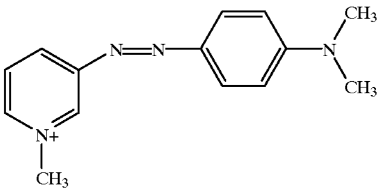
$CH_3SO_4^-$
(I)38
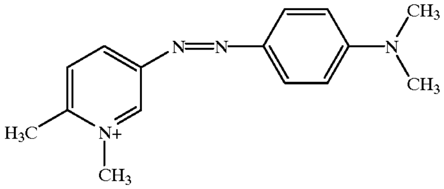
$CH_3SO_4^-$
(I)39
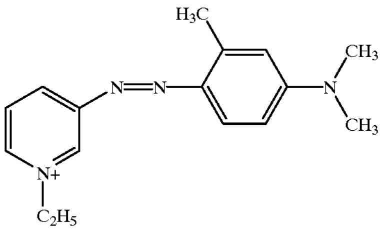
$C_2H_5SO_4^-$
(I)40
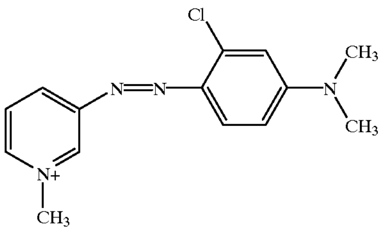
$CH_3SO_4^-$
(I)41
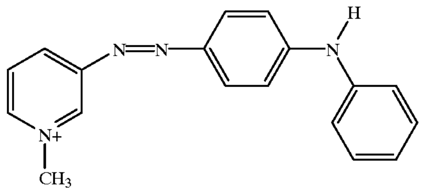
$CH_3SO_4^-$
(I)42
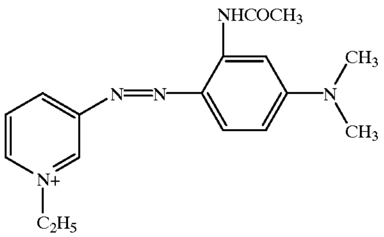
$C_2H_5SO_4^-$
-continued
(I)43
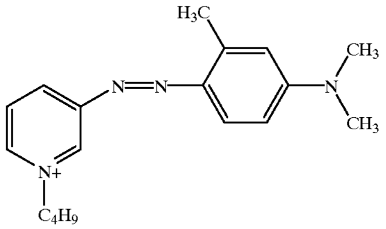
$Br^-$
(I)44
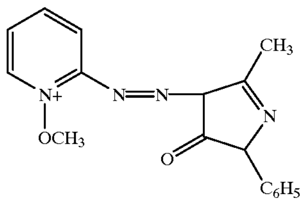
$CH_3SO_4^-$
(I)45
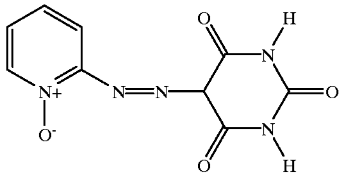
(I)46
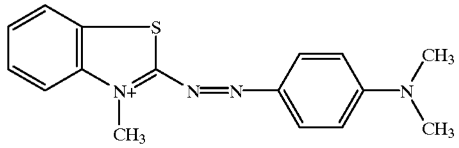
$ClO_4^-$
(I)47
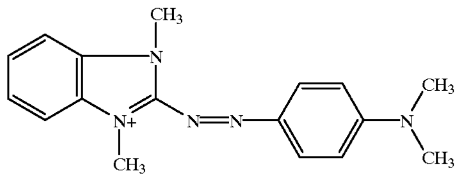
$ClO_4^-$
(I)48
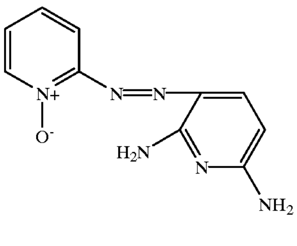
(I)49
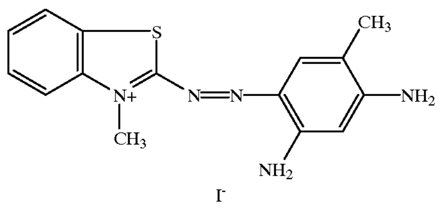
$I^-$ -continued
(I)50
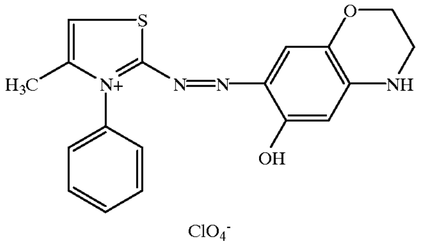
(I)51
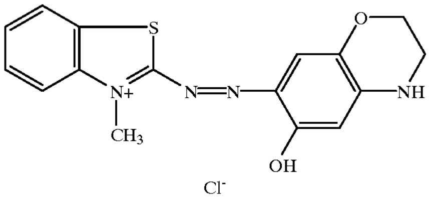
(I)52
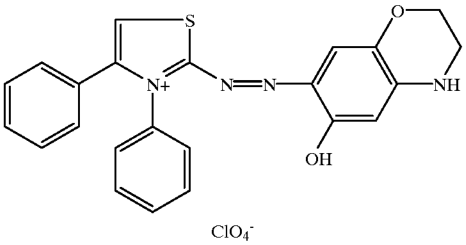
(I)53
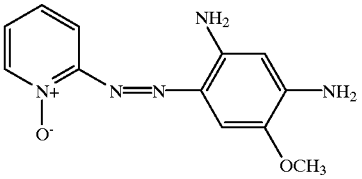
(I)54
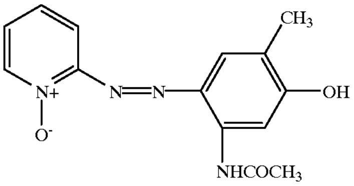
(I)55
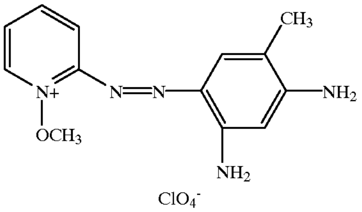
(I)56
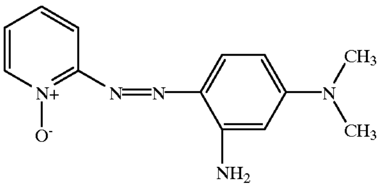
-continued
(I)57
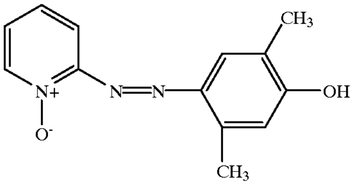
(I)58
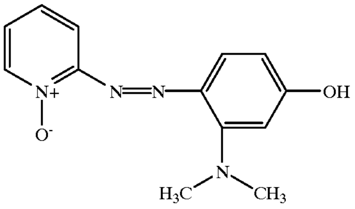
(I)59
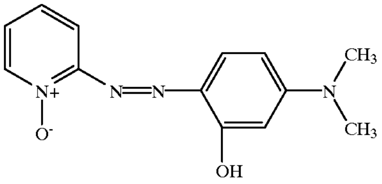
(I)60
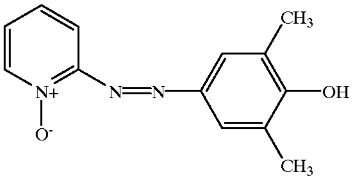
(I)61
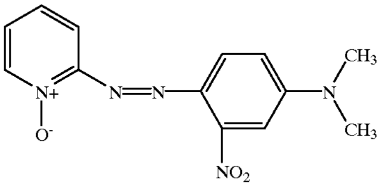
(I)62
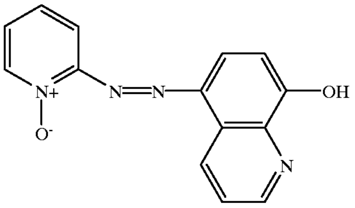
(I)63
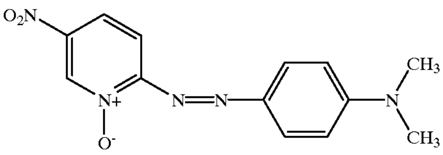

-continued
(I)64
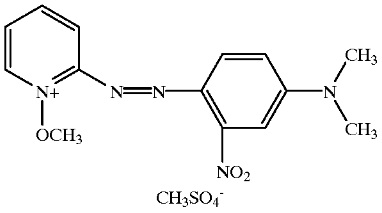
(I)65
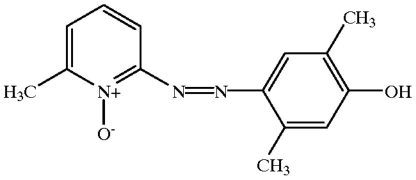
(I)66
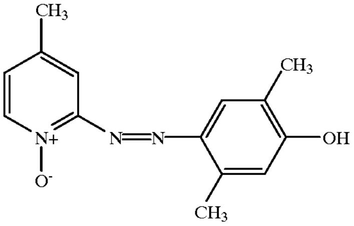
(I)67
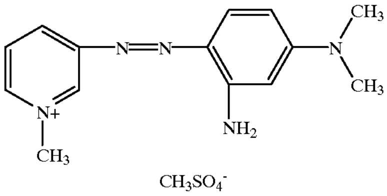
(I)68
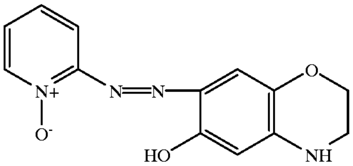
(I)69
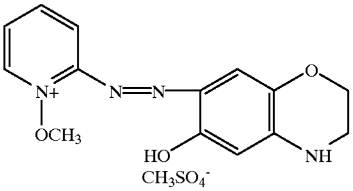
(I)70
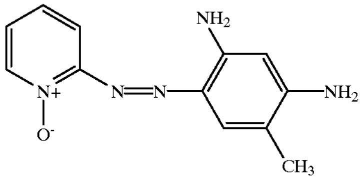
-continued
(I)71
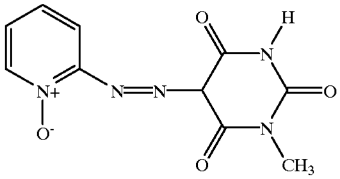
(I)72
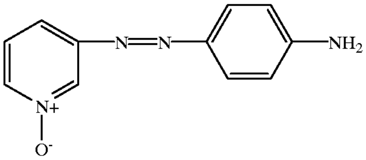
(I)73
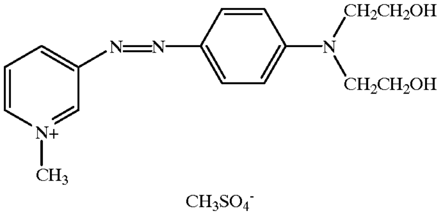
(I)74
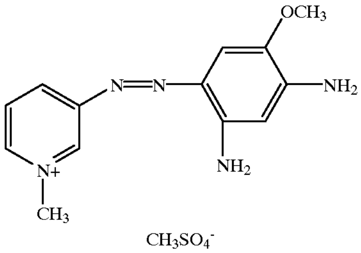
(I)75
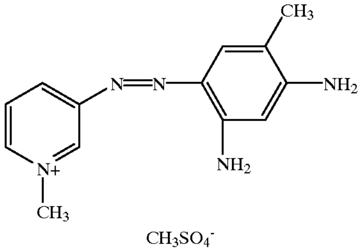
(I)76
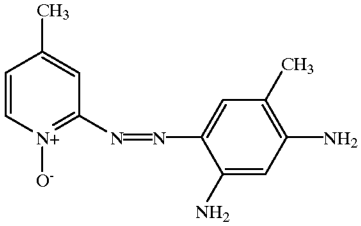
(I)77
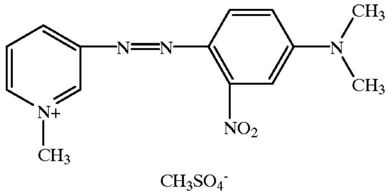

The cationic direct dye(s) used according to the invention preferably represent(s) from 0.001 to 10% by weight approximately relative to the total weight of the dye composition, and even more preferably from 0.005 to 5% by weight approximately relative to this weight.

(ii) For the purposes of the invention, the term "polyol" denotes a compound of linear, branched or cyclic, saturated or unsaturated alkyl type bearing at least two —OH functions on the alkyl chain, as well as the polymers (polyethers) of these polyhydroxyalkyl compounds.

The specific polyols used according to the invention contain at least 4 carbon atoms and can be chosen in particular from $C_4$–$C_9$ polyols and polyalkylene glycols such as, more particularly, polyethylene glycols and polypropylene glycols.

Among the $C_4$–$C_9$ polyols, mention may be made in particular of 2-butene-1,4-diol, pentane-1,5-diol, 2,2-dimethylpropane-1,3-diol, 3-methylpentane-1,5-diol, pentane-1,2-diol, 2,2,4-trimethylpentane-1,3-diol, 2-methylpropane-1,3-diol, hexylene glycol, 1,3-butylene glycol, dipropylene glycol, diethylene glycol and triethylene glycol.

The specific polyol ethers according to the invention are chosen from $C_1$–$C_8$ aliphatic ethers of $C_3$–$C_9$ polyols and $C_6$–$C_8$ aromatic ethers of $C_2$–$C_9$ polyols.

Among the $C_1$–$C_8$ aliphatic ethers of $C_3$–$C_9$ polyols, mention may be made in particular of propylene glycol monomethyl ether, propylene glycol monoethyl ether, isopropylene glycol dimethyl ether, diethylene glycol monomethyl ether and monoethyl ether, dipropylene glycol monomethyl ether, tripropylene glycol monomethyl ether and diethylene glycol dimethyl ether;

among the $C_6$–$C_8$ aromatic ethers of $C_2$–$C_9$ polyols, mention may be made in particular of ethylene glycol monophehyl ether, ethylene glycol monobenzyl ether, propylene glycol monophenyl ether, propylene glycol monobenzyl ether, diethylene glycol monophenyl ether and diethylene glycol monobenzyl ether.

The glycerol and/or the polyol(s) and/or polyol ether(s) described for the purposes of the invention are present in the dye composition in accordance with the invention in proportions generally ranging from 0.1 to 40% by weight, and even more particularly from 0.5 to 20% by weight, relative to the total weight of the composition.

The medium which is suitable for dyeing (or support) generally comprises a mixture of water and at least glycerol and/or a polyol and/or polyol ether as defined above. It can also contain one or more organic solvents other than glycerol and/or the polyol(s) and/or polyol ether(s) used in accordance with the invention, to dissolve the compounds which would not be sufficiently soluble in water. Organic solvents which may be mentioned, for example, are $C_1$–$C_4$ alkanols such as ethanol and isopropanol, as well as aromatic alcohols such as benzyl alcohol, similar products and mixtures thereof.

The said additional organic solvents can be present in proportions preferably approximately ranging from 0.5 to 40% by weight relative to the total weight of the dye composition, and even more preferably approximately from 1 to 20% by weight.

The pH of the dye composition in accordance with the invention generally approximately ranges from 2 to 11, and preferably approximately from 5 to 10. It can be adjusted to the desired value using acidifying or basifying agents usually used for also dyeing keratin fibers.

Among the acidifying agents which may be mentioned, for example, are inorganic or organic acids such as hydrochloric acid, orthophosphoric acid, sulphuric acid, carboxylic acids such as acetic acid, tartaric acid, citric acid or lactic acid, and sulphonic acids.

Among the basifying agents which may be mentioned, for example, are aqueous ammonia, alkaline carbonates, alkanolamines such as mono-, di- and triethanolamine and derivatives thereof, sodium hydroxide, potassium hydroxide and the compounds of formula (II) below:

(II)

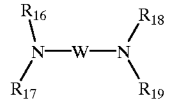

in which W is a propylene residue optionally having a substituent chosen from a hydroxyl group and $C_1$–$C_6$ alkyl radicals; $R_{16}$, $R_{17}$, $R_{18}$ and $R_{19}$, which may be identical or different, are chosen from a hydrogen atom and $C_1$–$C_6$ alkyl and $C_1$–$C_6$ hydroxyalkyl radicals.

In addition to the cationic direct dye(s) defined above, the dye composition in accordance with the invention can contain one or more additional direct dyes which may be chosen, for example, from nitrobenzene dyes, anthraquinone dyes, naphthoquinone dyes, triarylmethane dyes, xanthene dyes and azo dyes which are non-cationic.

When it is intended for oxidation dyeing, in addition to the cationic direct dye(s) and glycerol and/or specific polyol and/or polyol ether defined above, the dye composition in accordance with the invention contains one or more oxidation bases chosen from the oxidation bases conventionally used for oxidation dyeing and among which mention may be made in particular of para-phenylenediamines, bis(phenyl) alkylenediamines, para-aminophenols, ortho-aminophenols and heterocyclic bases.

When it is (they are) used, the oxidation base(s) preferably represent(s) from 0.0005 to 12% by weight approximately relative to the total weight of the dye composition, and even more preferably from 0.005 to 6% by weight approximately relative to this weight.

When it is intended for oxidation dyeing, in addition to the cationic direct dye and glycerol and/or specific polyol and/or polyol ether defined above as well as oxidation bases, the dye composition in accordance with the invention can also contain one or more couplers so as to modify or enrich with glints the shades obtained using the cationic direct dye(s) and the oxidation bases.

The couplers which can be used in the dye composition in accordance with the invention can be chosen from the couplers used conventionally in oxidation dyeing and among which mention may be made in particular of meta-phenylenediamines, meta-aminophenols, meta-diphenols and heterocyclic couplers.

When it is (they are) present, the coupler(s) preferably represent(s) from 0.0001 to 10% by weight approximately relative to the total weight of the dye composition, and even more preferably from 0.005 to 5% by weight approximately relative to this weight.

The dye composition in accordance with the invention can also contain various adjuvants conventionally used in compositions for dyeing the hair, such as antioxidants, penetrating agents, sequestering agents, fragrances, buffers, dispersing agents, surfactants, film-forming agents, ceramides, preserving agents, screening agents and opacifiers.

Needless to say, a person skilled in the art will take care to select this or these optional complementary compound(s) such that the advantageous properties intrinsically associated with the dye composition in accordance with the invention are not, or are not substantially, adversely affected by the addition(s) envisaged.

The dye composition according to the invention can be in various forms, such as in the form of liquids, shampoos, creams or gels or any other form which is suitable for dyeing keratin fibers, and in particular human hair. It can be obtained by mixing, at the time of use, a composition, which may be in pulverulent form, containing the cationic direct dye(s) with a composition containing the glycerol and/or the specific polyol and/or polyol ether.

When the combination of the cationic direct dye and glycerol and/or specific polyol and/or polyol ether defined according to the invention is used in a composition intended for oxidation dyeing (one or more oxidation bases are then used, optionally in the presence of one or more couplers), or when it is used in a composition intended for lightening direct dyeing, then the dye composition in accordance with the invention also contains at least one oxidizing agent chosen, for example, from hydrogen peroxide, urea peroxide, alkali metal bromates, persalts such as perborates and persulphates, and enzymes such as peroxidases, laccases and two-electron oxidoreductases. The use of hydrogen peroxide or enzymes is particularly preferred.

Another subject of the invention is a process for dyeing keratin fibers, and in particular human keratin fibers such as the hair, using the dye composition as defined above.

According to a first variant of this dyeing process in accordance with the invention, at least one dye composition as defined above is applied to the fibers, for a period which is sufficient to develop the desired coloration, after which the fibers are rinsed, optionally washed with shampoo, rinsed again and dried.

The time required to develop the coloration on the keratin fibers generally ranges from 3 to 60 minutes and even more preferably from 5 to 40 minutes.

According to a second variant of this dyeing process in accordance with the invention, at least one dye composition as defined above is applied to the fibers, for a period which is sufficient to develop the desired coloration, without final rinsing.

According to one specific embodiment of this dyeing process, and when the dye composition in accordance with the invention contains at least one oxidation base and at least one oxidizing agent, the dyeing process includes a preliminary step which comprises separately storing, on the one hand, a composition (A1) comprising, in a medium which is suitable for dyeing, at least one cationic direct dye and at least glycerol and/or one specific polyol and/or polyol ether as defined above and at least one oxidation base, and, on the other hand, a composition (B1) containing, in a medium which is suitable for dyeing, at least one oxidizing agent, and then in mixing them together at the time of use, after which this mixture is applied to the keratin fibers.

According to another specific embodiment of this dyeing process, and when the dye composition in accordance with the invention contains at least one oxidizing agent, the dyeing process includes a preliminary step which comprises separately storing, on the one hand, a composition (A2) comprising, in a medium which is suitable for dyeing, at least one cationic direct dye and at least glycerol and/or one specific polyol and/or polyol ether as defined above, and, on the other hand, a composition (B1) containing, in a medium which is suitable for dyeing, at least one oxidizing agent, and then in mixing them together at the time of use, after which this mixture is applied to the keratin fibers.

Another subject of the invention is a multi-compartment dyeing device or "kit" or any other multi-compartment packaging system, a first compartment of which comprises composition (A1) or (A2) as defined above and a second compartment of which comprises composition (B1) as defined above. These devices can be equipped with means for delivering the desired mixture onto the hair, such as the devices described in patent FR 2,586,913, assigned to the present assignee.

The examples which follow are intended to illustrate the invention without, however, limiting its scope.

EXAMPLES

Example 1

| The dye composition below was prepared: | |
|---|---|
| Cationic direct dye of formula $(I)_{27}$ | 0.1 g |
| Glycerol | 10.0 g |
| 2-Amino-2-methylpropanol | qs pH9 |
| Demineralized water | qs 100 g |
| A.M.*: Active material | |

The above composition was applied for 30 minutes to locks of natural grey hair containing 90% white hairs. The locks of hair were then rinsed, washed with a standard shampoo and then dried.

They were dyed in an intense purple shade.

Example 2

| The dye composition below was prepared: | |
|---|---|
| Cationic direct dye of formula $(I)_{10}$ | 0.12 g |
| Propylene glycol monomethyl ether | 10.0 g |
| 2-Amino-2-methylpropanol | qs pH9 |
| Demineralized water | qs 100 g |
| A.M.*: Active material | |

The above composition was applied for 30 minutes to locks of natural grey hair containing 90% white hairs. The locks of hair were then rinsed, washed with a standard shampoo and then dried.

They were dyed in an intense red shade.

What is claimed is:

1. A composition for dyeing keratin fibers comprising:

(i) at least one cationic direct dye of formula (I) below:

$$A—N{=}N—B \qquad (I)$$

in which:

the symbol A represents a group chosen from structures $A_1$ to $A_3$ below:

$A_1$

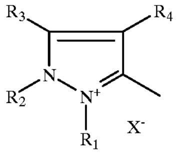

-continued

A2

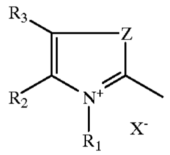

A3

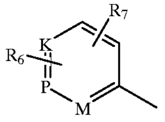

in which structures $A_1$ to $A_3$, $R_1$ is chosen from $C_1$–$C_4$ alkyl radicals and a phenyl radical having a substituent chosen from $C_1$–$C_4$ alkyl radicals and halogen atoms chosen from chlorine, bromine, iodine and fluorine;

$R_2$ is chosen from $C_1$–$C_4$ alkyl radicals and a phenyl radical; $R_3$ and $R_4$, which may be identical or different, are chosen from $C_1$–$C_4$ alkyl radicals and a phenyl radical and, in the case of structure $A_1$, can together form a substituted benzene ring, and in the case of structure $A_2$, can together form a benzene ring optionally having at least one substituent chosen from $C_1$–$C_4$ alkyl, $C_1$–$C_4$ alkoxy and $NO_2$ radicals;

$R_3$ can also denote a hydrogen atom;

Z is chosen from an oxygen atom, a sulphur atom, and —$NR_2$ groups;

M is chosen from —CH, —CR, where R is chosen from $C_1$–$C_4$ alkyl radicals, and —$N^+R_5(X^-)_r$ groups;

K is chosen from —CH, —CR, where R is chosen from $C_1$–$C_4$ alkyl radicals, and —$N^+R_5(X^-)_r$ groups;

P is chosen from —CH, —CR, where R is chosen from $C_1$–$C_4$ alkyl radicals, and —$N^+R_5(X^-)_r$ groups;

r denotes 0 or 1;

$R_5$ is chosen from an atom $O^-$, $C_1$–$C_4$ alkoxy radicals and $C_1$–$C_4$ alkyl radicals;

$R_6$ and $R_7$, which may be identical or different, are chosen from a hydrogen atom, halogen atoms chosen from chlorine, bromine, iodine and fluorine, $C_1$–$C_4$ alkyl radicals, $C_1$–$C_4$ alkoxy radicals and an —$NO_2$ radical;

$X^-$is an anion;

with the proviso that, if $R_4$ is a $C_1$–$C_4$ alkyl radical and Z is a sulphur atom, $R_3$ is not a hydrogen atom;

if $R_5$ is $O^-$, then r is zero;

if K or P or M is —$N^+$—$C_1$–$C_4$ -alkyl $X^-$, then $R_6$ or $R_7$ is other than a hydrogen atom;

if K is —$N^+R_5(X^-)_r$, then M═P and is —CH or —CR;

if M is —$N^+R_5(X^-)_r$, then K═P and is —CH or —CR;

if P is —$N^+R_5(X^-)_r$, then K=M and is —CH or —CR;

at least one of K, M, and P is —$N^+R_5(X^-)_r$;

if Z is —$NR_2$ and $R_2$ is a $C_1$–$C_4$ alkyl radical, then at least one of the radicals $R_1$, $R_3$ or $R_4$ of structure $A_2$ is other than a $C_1$–$C_4$ alkyl radical;

the symbol B represents:

(a) a group of structure $B_1$ below:

B1

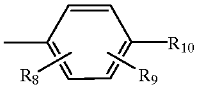

in which structure $B_1$, $R_8$ is chosen from a hydrogen atom, halogen atoms chosen from chlorine, bromine, iodine and fluorine, $C_1$–$C_4$ alkyl radicals, $C_1$–$C_4$ alkoxy radicals, a radical —OH, a radical —$NO_2$, —$NHR_{11}$ radicals, —$NR_{12}R_{13}$ radicals, and —NHCO($C_1$–$C_4$)alkyl radicals or forms, with $R_9$, a 5- or 6-membered ring which may contain at least one hetero atom chosen from nitrogen, oxygen and sulphur;

$R_9$ is chosen from a hydrogen atom, halogen atoms chosen from chlorine, bromine, iodine and fluorine, $C_1$–$C_4$ alkyl radicals, and $C_1$–$C_4$ alkoxy radicals, or forms, with $R_{10}$ or $R_{11}$, a 5- or 6-membered ring which may contain at least one hetero atom chosen from nitrogen, oxygen and sulphur;

$R_{10}$ is chosen from a hydrogen atom, an —OH radical, —$NHR_{11}$ radicals and —$NR_{12}R_{13}$ radicals;

$R_{11}$ is chosen from a hydrogen atom, $C_1$–$C_4$ alkyl radicals, $C_1$–$C_4$ monohydroxyalkyl radicals, $C_2$–$C_4$ polyhydroxyalkyl radicals and a phenyl radical;

$R_{12}$ and $R_{13}$, which may be identical or different, are chosen from $C_1$–$C_4$ alkyl radicals, $C_1$–$C_4$ monohydroxyalkyl radicals and $C_2$–$C_4$ polyhydroxyalkyl radicals; or (b) a 5- or 6-membered nitrogenous heterocyclic group which can contain at least one other hetero atom and/or at least one carbonyl group and which can have at least one substituent chosen from $C_1$–$C_4$ alkyl, amino and phenyl radicals, and (ii) at least one compound chosen from glycerol, polyols containing at least 4 carbon atoms, $C_1$–$C_8$ aliphatic ethers of $C_3$–$C_9$ polyols, and $C_6$–$C_8$ aromatic ethers of $C_2$–$C_9$ polyols.

2. The composition according to claim 1, wherein, in formula (I), the $C_1$–$C_4$ alkyl radicals are chosen from methyl, ethyl, and butyl radicals and the $C_1$–$C_4$ alkoxy radicals are methoxy and ethoxy radicals.

3. The composition according to claim 1, wherein the symbol B represents a a group of structure $B_2$ below:

B2

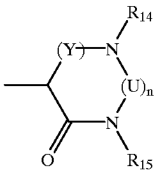

in which structure $B_2$, $R_{14}$ and $R_{15}$, which may be identical or different, are chosen from a hydrogen atom, $C_1$–$C_4$ alkyl radicals and a phenyl radical;

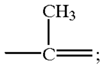

Y is chosen from a —CO— radical and a radical n=0 or 1, where, when n is 1, U is a —CO— radical.

4. The composition according to claim 1, wherein $X^-$is chosen from chloride, iodide, methyl sulphate, ethyl sulphate, acetate and perchlorate.

5. The composition according to claim 1, wherein said keratin fibers are human keratin fibers.

6. The composition according to claim 5, wherein said human keratin fibers are hair.

7. The composition according to claim 1, wherein said polyols containing at least 4 carbon atoms are chosen from $C_4$–$C_9$ polyols and polyalkylene glycols.

8. The composition according to claim 7, wherein said polyalkylene glycols are chosen from polyethylene glycols and polypropylene glycols.

9. The composition according to claim 7, wherein said $C_4$–$C_9$ polyols are chosen from 2-butene-1,4-diol pentane-1,5-diol, 2,2-dimethylpropane-1,3-diol, 3-methylpentane-1,5-diol, pentane-1,2-diol, 2,2,4-trimethylpentane-1,3-diol, 2-methylpropane-1,3-diol, hexylene glycol, 1,3-butylene glycol, dipropylene glycol, diethylene glycol and triethylene glycol.

10. The composition according to claim 1, wherein said $C_1$–$C_8$ aliphatic ethers of $C_3$–$C_9$ polyols are chosen from propylene glycol monomethyl ether, propylene glycol monoethyl ether, isopropylene glycol dimethyl ether, diethylene glycol monomethyl ether and monoethyl ether, dipropylene glycol monomethyl ether, tripropylene glycol monomethyl ether and diethylene glycol dimethyl ether.

11. The composition according to claim 1, wherein said $C_6$–$C_8$ aromatic ethers of $C_2$–$C_9$ polyols are chosen from ethylene glycol monophenyl ether, ethylene glycol monobenzyl ether, propylene glycol monophenyl ether, propylene glycol monobenzyl ether, diethylene glycol monophenyl ether and diethylene glycol monobenzyl ether.

12. The composition according to claim 1, wherein said at least one cationic direct dye of formula (I) is present in an amount ranging from 0.001 to 10% by weight relative to the total weight of the composition.

13. The composition according to claim 1, wherein said at least one cationic direct dye of formula (I) is present in an amount ranging from 0.005 to 5% by weight relative to the total weight of the composition.

14. The composition according to claim 1, wherein said at least one compound chosen from glycerol, polyols containing at least 4 carbon atoms, $C_1$–$C_8$ aliphatic ethers of $C_3$–$C_9$polyols and $C_6$–$C_8$ aromatic ethers of $C_2$–$C_9$ polyols is present in an amount ranging from 0.1 to 40% by weight relative to the total weight of the composition.

15. The composition according to claim 14, herein said at least one compound is present in an amount ranging from 0.5 to 20% by weight relative to the total weight of the composition.

16. The composition according to claim 1, wherein said composition further comprises additional direct dyes.

17. The composition according to claim 1, wherein said composition further comprises a mixture of water and at least one solvent chosen from glycerol, polyols containing at least 4 carbon atoms, $C_1$–$C_8$ aliphatic ethers of $C_3$–$C_9$ polyols, and $C_6$–$C_8$ aromatic ethers of $C_2$–$C_9$ polyols.

18. The composition according to claim 17, wherein said composition further comprises at least one additional organic solvent.

19. The composition according to claim 1, wherein said composition has a pH ranging from 2 to 11.

20. The composition according to claim 19, wherein said pH ranges from 5 to 10.

21. The composition according to claim 1, wherein said composition further comprises at least one oxidation base chosen from para-phenylenediamines, bis(phenyl) alkylenediamines, para-aminophenols, ortho-aminophenols and heterocyclic bases.

22. The composition according to claim 21, wherein said at least one oxidation base is present in ah amount ranging from 0.0005 to 12% by weight relative to the total weight of the composition.

23. The composition according to claims 22, wherein said at least one oxidation base is present in an amount ranging from 0.005 to 6% by weight relative to the total weight of the composition.

24. The composition according to claim 21, wherein said composition further comprises at least one coupler chosen from meta-phenylenediamine, meta-aminophenols, meta-diphenols and heterocyclic couplers.

25. The composition according to claim 24, wherein said at least one coupler is present in an amount ranging from 0.0001 to 10% by weight relative to the total weight of the composition.

26. The composition according to claim 25, wherein said at least one coupler is present in an amount ranging from 0.005 to 5% by weight relative to the total weight of the composition.

27. The composition according to claim 1, wherein said composition further comprises at least one oxidizing agent.

28. A process for dyeing keratin fibers, comprising applying to said fibers, for a period which is sufficient to develop a desired coloration, at least one dye composition comprising:

(i) at least one cationic direct dye of formula (I) below:

A—N═N—B (I)

in which:

the symbol A represents a group chosen from structures $A_1$ to $A_3$ below:

$A_1$

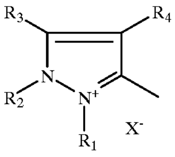

$A_2$

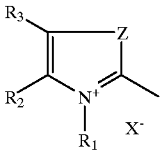

$A_3$

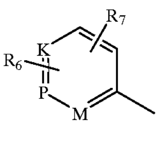

in which structures $A_1$ to $A_3$, $R_1$ is chosen from $C_1$–C4 alkyl radicals and a phenyl radical having a substituent chosen from $C_1$–$C_4$ alkyl radicals and halogen atoms chosen from chlorine, bromine, iodine and fluorine;

$R_2$ is chosen from $C_1$–C4 alkyl radicals and a phenyl radical;

$R_3$ and $R_4$, which may be identical or different, are chosen from $C_1$–$C_4$ alkyl radicals and a phenyl radical and, in the case of structure $A_1$, can together form a substituted benzene ring, and in the case of structure $A_2$, can together form a benzene ring optionally having at least one substituent chosen from $C_1$–$C_4$ alkyl, $C_1$–$C_4$ alkoxy and $NO_2$ radicals;

$R_3$ can also denote a hydrogen atom;

Z is chosen from an oxygen atom, a sulphur atom, and —$NR_2$ groups;

M is chosen from —CH, —CR, where R is chosen from $C_1$–$C_4$ alkyl radicals, and —$N^+R_5(X^-)_r$ groups;

K is chosen from —CH, —CR, where R is chosen from $C_1$–$C_4$ alkyl radicals, and —$N^+R_5(X^-)_r$ groups;

P is chosen from —CH, —CR, where R is chosen from $C_1$–$C_4$ alkyl radicals, and —$N^+R_5(X^-)_r$ groups;

r denotes 0 or 1;

$R_5$ is chosen from an atom $O^-$, $C_1$–$C_4$ alkoxy radicals and $C_1$–$C_4$ alkyl radicals;

$R_6$ and $R_7$, which may be identical or different, are chosen from a hydrogen atom, halogen atoms chosen from chlorine, bromine, iodine and fluorine, $C_1$–$C_4$ alkyl radicals, $C_1$–$C_4$ alkoxy radicals and an —$NO_2$ radical;

$X^-$ is an anion;

with the proviso that, if $R_4$ is a $C_1$–$C_4$ alkyl radical and Z is a sulphur atom, $R_3$ is not a hydrogen atom;

if $R_5$ is $O^-$, then r is zero;

if K or P or M is —$N^+$—$C_1$–$C_4$-alkyl $X^-$, then $R_6$ or $R_7$ is other than a hydrogen atom;

if K is —$N^+R_5(X^-)_r$, then M═P and is —CH or —CR;

if M is —$N^+R_5(X^-)_r$, then K═P and is —CH or —CR;

if P is —$N^+R_5(X^-)_r$, then K=M and is —CH or —CR;

at least one of K, M, and P is —$N^+R_5(X^-)_r$;

if Z is —$NR_2$ and $R_2$ is a $C_1$–$C_4$ alkyl radical, then at least one of the radicals $R_1$, $R_3$ or $R_4$ of structure $A_2$ is other than a $C_1$–$C_4$ alkyl radical;

the symbol B represents:

(a) a group of structure $B_1$ below:

$B_1$

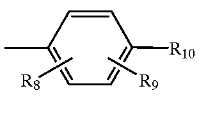

in which structure $B_1$, $R_8$ is chosen from a hydrogen atom, halogen atoms chosen from chlorine, bromine, iodine and fluorine, $C_1$–$C_4$ alkyl radicals, $C_1$–$C_4$ alkoxy radicals, a radical —OH, a radical —$NO_2$, —$NHR_{11}$ radicals, —$NR_{12}R_{13}$ radicals, and —$NHCO(C_1$–$C_4)$alkyl radicals or forms, with $R_9$, a 5- or 6-membered ring which may contain at least one hetero atom chosen from nitrogen, oxygen and sulphur;

$R_9$ is chosen from a hydrogen atom, halogen atoms chosen from chlorine, bromine, iodine and fluorine, $C_1$–$C_4$ alkyl radicals, and $C_1$–$C_4$ alkoxy radicals, or forms, with $R_{10}$ or $R_{11}$, a 5- or 6-membered ring which may contain at least one hetero atom chosen from nitrogen, oxygen and sulphur;

$R_{10}$ is chosen from a hydrogen atom, an —OH radical, —$NHR_{11}$ radicals and —$NR_{12}R_{13}$ radicals;

$R_{11}$ is chosen from a hydrogen atom, $C_1$–$C_4$ alkyl radicals, $C_1$–$C_4$ monohydroxyalkyl radicals, $C_2$–$C_4$ polyhydroxyalkyl radicals and a phenyl radical;

$R_{12}$ and $R_{13}$, which may be identical or different, are chosen from $C_1$–$C_4$ alkyl radicals, $C_1$–$C_4$ monohydroxyalkyl radicals and $C_2$–$C_4$ polyhydroxyalkyl radicals; or (b) a 5- or 6-membered nitrogenous heterocyclic group which can contain at least one other hetero atom and/or at least one carbonyl group and which can have at least one substituent chosen from $C_1$–$C_4$ alkyl, amino and phenyl radicals, and (ii) at least one compound chosen from glycerol, polyols containing at least 4 carbon atoms, $C_1$–$C_8$ aliphatic ethers of $C_3$–$C_9$ polyols, and $C_6$–$C_8$ aromatic ethers of $C_2$–$C_9$ polyols, rinsing the fibers a first time, optionally washing said fibers with shampoo, rinsing said fibers a second time, and drying.

29. A process for dyeing keratin fibers according to claim 28, wherein said keratin fibers are human keratin fibers.

30. A process for dyeing keratin fibers according to claim 29, wherein said human keratin fibers are hair.

31. A process for dyeing keratin fibers comprising:

separately storing a first composition comprising:

(i) at least one cationic direct dye of formula (I) below:

$$A—N{=}N—B \qquad (I)$$

in which:

the symbol A represents a group chosen from structures $A_1$ to $A_3$ below:

$A_1$

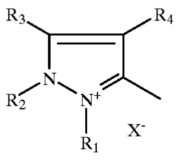

$A_2$

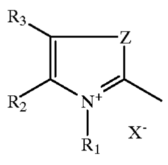

-continued

A3

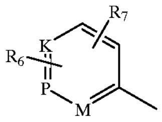

in which structures $A_1$ to $A_3$, $R_1$ is chosen from $C_1$–$C_4$ alkyl radicals and a phenyl radical having a substituent chosen from $C_1$–$C_4$ alkyl radicals and halogen atoms chosen from chlorine, bromine, iodine and fluorine;

$R_2$ is chosen from $C_1$–$C_4$ alkyl radicals and a phenyl radical;

$R_3$ and $R_4$, which may be identical or different, are chosen from $C_1$–$C_4$ alkyl radicals and a phenyl radical and, in the case of structure $A_1$, can together form a substituted benzene ring, and in the case of structure $A_2$, can together form a benzene ring optionally having at least one substituent chosen from $C_1$–$C_4$ alkyl, $C_1$–$C_4$ alkoxy and $NO_2$ radicals;

$R_3$ can also denote a hydrogen atom;

Z is chosen from an oxygen atom, a sulphur atom, and —$NR_2$ groups;

M is chosen from —CH, —CR, where R is chosen from $C_1$–$C_4$ alkyl radicals, and —$N^+R_5$ $(X^-)_r$ groups;

K is chosen from —CH, —CR, where R is chosen from $C_1$–$C_4$ alkyl radicals, and —$N^+R_5$ $(X^-)_r$ groups;

P is chosen from —CH, —CR, where R is chosen from $C_1$–$C_4$ alkyl radicals, and —$N^+R_5(X^-)_r$ groups;

r denotes 0 or 1;

$R_5$ is chosen from an atom $O^-$, $C_1$–$C_4$ alkoxy radicals and $C_1$–$C_4$ alkyl radicals;

$R_6$ and $R_7$, which may be identical or different, are chosen from a hydrogen atom, halogen atoms chosen from chlorine, bromine, iodine and fluorine, $C_1$–$C_4$ alkyl radicals, $C_1$–$C_4$ alkoxy radicals and an —$NO_2$ radical;

$X^-$is an anion;

with the proviso that, if $R_4$ is a $C_1$–$C_4$ alkyl radical and Z is a sulphur atom, $R_3$ is not a hydrogen atom;

if $R_5$ is $O^-$, then r is zero;

if K or P or M is —$N^+$—$C_1$–$C_4$ -alkyl $X^-$, then $R_6$ or $R_7$ is other than a hydrogen atom;

if K is —$N^+R_5(X^-)_r$, then M═P and is —CH or —CR;

if M is —$N^+R_5(X^-)_r$, then K═P and is —CH or —CR;

if P is —$N^+R_5(X^-)_r$, then K═M and is —CH or —CR;

at least one of K, M, and P is —$N^+R_5(X^-)_r$;

if Z is —$NR_2$ and $R_2$ is a $C_1$–$C_4$ alkyl radical, then at least one of the radicals $R_1$, $R_3$ or $R_4$ of structure $A_2$ is other than a $C_1$–$C_4$ alkyl radical;

the symbol B represents:

(a) a group of structure $B_1$ below:

B1

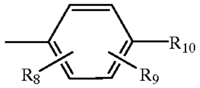

in which structure $B_1$, $R_8$ is chosen from a hydrogen atom, halogen atoms chosen from chlorine, bromine, iodine and fluorine, $C_1$–$C_4$ alkyl radicals, $C_1$–$C_4$ alkoxy radicals, a radical —OH, a radical —$NO_2$, —$NHR_{11}$ radicals, —$NR_{12}R_{13}$ radicals, and —NHCO($C_1$–$C_4$)alkyl radicals or forms, with $R_9$, a 5- or 6-membered ring which may contain at least one hetero atom chosen from nitrogen, oxygen and sulphur;

$R_9$ is chosen from a hydrogen atom, halogen atoms chosen from chlorine, bromine, iodine and fluorine, $C_1$–$C_4$ alkyl radicals, and $C_1$–$C_4$ alkoxy radicals, or forms, with $R_{10}$ or $R_{11}$, a 5- or 6-membered ring which may contain at least one hetero atom chosen from nitrogen, oxygen and sulphur;

$R_{10}$ is chosen from a hydrogen atom, an —OH radical, —$NHR_{11}$ radicals and —$NR_{12}R_{13}$ radicals;

$R_{11}$ is chosen from a hydrogen atom, $C_1$–$C_4$ alkyl radicals, $C_1$–$C_4$ monohydroxyalkyl radicals, $C_2$–$C_4$ polyhydroxyalkyl radicals and a phenyl radical;

$R_{12}$ and $R_{13}$, which may be identical or different, are chosen from $C_1$–$C_4$ alkyl radicals, $C_1$–$C_4$ monohydroxyalkyl radicals and $C_2$–$C_4$ polyhydroxyalkyl radicals; or (b) a 5- or 6-membered nitrogenous heterocyclic group which can contain at least one other hetero atom and/or at least one carbonyl group and which can have at least one substituent chosen from $C_1$–$C_4$ alkyl, amino and phenyl radicals, and (ii) at least one compound chosen from glycerol, polyols containing at least 4 carbon atoms, $C_1$–$C_8$ aliphatic ethers of $C_3$–$C_9$ polyols, and $C_6$–$C_8$ aromatic ethers of $C_2$–$C_9$ polyols, and (iii) at least one oxidation base, separately storing a second composition comprising at least one oxidizing agent, and thereafter mixing said first composition with said second composition and applying this mixture to said keratin fibers.

32. A process for dyeing keratin fibers comprising:

separately storing a first composition comprising (i) at least one cationic direct dye of formula (I) below:

$$A—N═N—B \qquad (I)$$

in which:

the symbol A represents a group chosen from structures $A_1$ to $A_3$ below:

A1

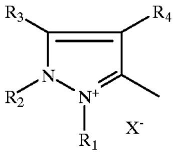

A2

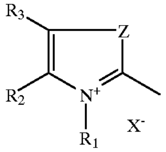

A3

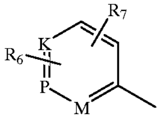

in which structures $A_1$ to $A_3$, $R_1$ is chosen from $C_1$–$C_4$ alkyl radicals and a phenyl radical having a substituent chosen from $C_1$–$C_4$ alkyl radicals and halogen atoms chosen from chlorine, bromine, iodine and fluorine;

$R_2$ is chosen from $C_1$–$C_4$ alkyl radicals and a phenyl radical;

$R_3$ and $R_4$, which may be identical or different, are chosen from $C_1$–$C_4$ alkyl radicals and a phenyl radical and, in the case of structure $A_1$, can together form a substituted benzene ring, and in the case of structure $A_2$, can together form a benzene ring optionally having at least one substituent chosen from $C_1$–$C_4$ alkyl, $C_1$–$C_4$ alkoxy and $NO_2$ radicals;

$R_3$ can also denote a hydrogen atom;

Z is chosen from an oxygen atom, a sulphur atom, and —$NR_2$ groups;

M is chosen from —CH, —CR, where R is chosen from $C_1$–$C_4$ alkyl radicals, and —$N^+R_5(X^-)_r$ groups;

K is chosen from —CH, —CR, where R is chosen from $C_1$–$C_4$ alkyl radicals, and —$N^+R_5(X^-)_r$ groups;

P is chosen from —CH, —CR, where R is chosen from $C_1$–$C_4$ alkyl radicals, and —$N^+R_5(X^-)_r$ groups;

r denotes 0 or 1;

$R_5$ is chosen from an atom $O^-$, $C_1$–$C_4$ alkoxy radicals and $C_1$–$C_4$ alkyl radicals;

$R_6$ and $R_7$, which may be identical or different, are chosen from a hydrogen atom, halogen atoms chosen from chlorine, bromine, iodine and fluorine, $C_1$–$C_4$ alkyl radicals, $C_1$–$C_4$ alkoxy radicals and an —$NO_2$ radical;

$X^-$ is an anion;

with the proviso that, if $R_4$ is a $C_1$–$C_4$ alkyl radical and Z is a sulphur atom, $R_3$ is not a hydrogen atom;

if $R_5$ is $O^-$, then r is zero;

if K or P or M is —$N^+$—$C_1$–$C_4$ -alkyl $X^-$, then $R_6$ or $R_7$ is other than a hydrogen atom;

if K is —$N^+R_5(X^-)_r$, then M═P and is —CH or —CR;

if M is —$N^+R_5(X^-)_r$, then K═P and is —CH or —CR;

if P is —$N^+R_5(X^-)_r$, then K═M and is —CH or —CR;

at least one of K, M, and P is —$N^+R_5(X^-)_r$;

if Z is —$NR_2$ and $R_2$ is a $C_1$–$C_4$ alkyl radical, then at least one of the radicals $R_1$, $R_3$ or $R_4$ of structure $A_2$ is other than a $C_1$–$C_4$ alkyl radical;

the symbol B represents:

(a) a group of structure $B_1$ below:

B1

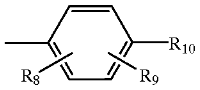

in which structure $B_1$, $R_8$ is chosen from a hydrogen atom, halogen atoms chosen from chlorine, bromine, iodine and fluorine, $C_1$–$C_4$ alkyl radicals, $C_1$–$C_4$ alkoxy radicals, a radical —OH, a radical —$NO_2$, —$NHR_{11}$ radicals, —$NR_{12}R_{13}$ radicals, and —NHCO($C_1$–$C_4$)alkyl radicals or forms, with $R_9$, a 5- or 6-membered ring which may contain at least one hetero atom chosen from nitrogen, oxygen and sulphur;

$R_9$ is chosen from a hydrogen atom, halogen atoms chosen from chlorine, bromine, iodine and fluorine, $C_1$–$C_4$ alkyl radicals, and $C_1$–$C_4$ alkoxy radicals, or forms, with $R_{10}$ or $R_{11}$, a 5- or 6-membered ring which may contain at least one hetero atom chosen from nitrogen, oxygen and sulphur;

$R_{10}$ is chosen from a hydrogen atom, an —OH radical, —$NHR_{11}$ radicals and —$NR_{12}R_{13}$ radicals;

$R_{11}$ is chosen from a hydrogen atom, $C_1$–$C_4$ alkyl radicals, $C_1$–$C_4$ monohydroxyalkyl radicals, $C_2$–$C_4$ polyhydroxyalkyl radicals and a phenyl radical;

$R_{12}$ and $R_{13}$, which may be identical or different, are chosen from $C_1$–$C_4$ alkyl radicals, $C_1$–$C_4$ monohydroxyalkyl radicals and $C_2$–$C_4$ polyhydroxyalkyl radicals; or (b) a 5- or 6-membered nitrogenous heterocyclic group which can contain at least one other hetero atom and/or at least one carbonyl group and which can have at least one substituent chosen from $C_1$–$C_4$ alkyl, amino and phenyl radicals, and (ii) at least one compound chosen from glycerol, polyols containing at least 4 carbon atoms, $C_1$–$C_8$ aliphatic ethers of $C_3$–$C_9$ polyols, and $C_6$–$C_8$ aromatic ethers of $C_2$–$C_9$ polyols, separately storing a second composition comprising at least one oxidizing agent, and thereafter mixing said first composition with said second composition and applying this mixture to said keratin fibers.

33. A multi-compartment dyeing device or multi-compartment dyeing kit comprising at least two separate compartments, wherein a first compartment contains a composition comprising:

(i) at least one cationic direct dye of formula (I) below:

(I)

A—N═N—B in which:

the symbol A represents a group chosen from structures $A_1$ to $A_3$ below:

$A_1$

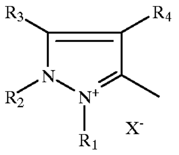

$A_2$

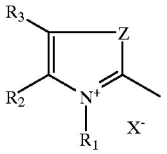

$A_3$

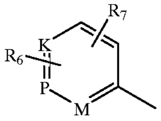

in which structures $A_1$ to $A_3$, $R_1$ is chosen from $C_1$–$C_4$ alkyl radicals and a phenyl radical having a substituent chosen from $C_1$–$C_4$ alkyl radicals and halogen atoms chosen from chlorine, bromine, iodine and fluorine;

$R_2$ is chosen from $C_1$–$C_4$ alkyl radicals and a phenyl radical;

$R_3$ and $R_4$ which may be identical or different, are chosen from $C_1$–$C_4$ alkyl radicals and a phenyl radical and, in the case of structure $A_1$, can together form a substituted benzene ring, and in the case of structure $A_2$, can together form a benzene ring optionally having at least one substituent chosen from $C_1$–$C_4$ alkyl, $C_1$–$C_4$ alkoxy and $NO_2$ radicals;

$R_3$ can also denote a hydrogen atom;

Z is chosen from an oxygen atom, a sulphur atom, and —$NR_2$ groups;

M is chosen from —CH, —CR, where R is chosen from $C_1$–$C_4$ alkyl radicals, and —$N^+R_5$ $(X^-)_r$ groups;

K is chosen from —CH, —CR, where R is chosen from $C_1$–$C_4$ alkyl radicals, and —$N^+R_5$ $(X^-)_r$ groups;

P is chosen from —CH, —CR, where R is chosen from $C_1$–$C_4$ alkyl radicals, and —$N^+R_5(X^-)_r$ groups;

r denotes 0 or 1;

$R_5$ is chosen from an atom $O^-$, $C_1$–$C_4$ alkoxy radicals and $C_1$–$C_4$ alkyl radicals;

$R_6$ and $R_7$, which may be identical or different, are chosen from a hydrogen atom, halogen atoms chosen from chlorine, bromine, iodine and fluorine, $C_1$–$C_4$ alkyl radicals, $C_1$–$C_4$ alkoxy radicals and an —$NO_2$ radical;

$X^-$ is an anion;

with the proviso that, if $R_4$ is a $C_1$–$C_4$ alkyl radical and Z is a sulphur atom, $R_3$ is not a hydrogen atom;

if $R_5$ is $O^-$, then r is zero;

if K or P or M is —$N^+$—$C_1$–$C_4$-alkyl $X^-$, then $R_6$ or $R_7$ is other than a hydrogen atom;

if K is —$N^+R_5(X^-)_r$, then M═P and is —CH or —CR;

if M is —$N^+R_5(X^-)_r$, then K═P and is —CH or —CR;

if P is —$N^+R_5(X^-)_r$, then K═M and is —CH or —CR;

at least one of K, M, and P is —$N^+R_5(X^-)_r$;

if Z is —$NR_2$ and $R_2$ is a $C_1$–$C_4$ alkyl radical, then at least one of the radicals $R_1$, $R_3$ or $R_4$ of structure $A_2$ is other than a $C_1$–$C_4$ alkyl radical;

the symbol B represents:

a) a group of structure $B_1$ below:

$B_1$

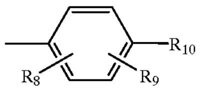

in which structure $B_1$, $R_8$ is chosen from a hydrogen atom, halogen atoms chosen from chlorine, bromine, iodine and fluorine, $C_1$–$C_4$ alkyl radicals, $C_1$–$C_4$ alkoxy radicals, a radical —OH, a radical —$NO_2$, —$NHR_{11}$ radicals, —$NR_{12}R_{13}$ radicals, and —$NHCO(C_1$–$C_4)$ alkyl radicals or forms, with $R_9$, a 5- or 6-membered ring which may contain at least one hetero atom chosen from nitrogen, oxygen and sulphur;

$R_9$ is chosen from a hydrogen atom, halogen atoms chosen from chlorine, bromine, iodine and fluorine, $C_1$–$C_4$ alkyl radicals, and $C_1$–$C_4$ alkoxy radicals, or forms, with $R_{10}$ or $R_{11}$, a 5- or 6-membered ring which may contain at least one hetero atom chosen from nitrogen, oxygen and sulphur;

$R_{10}$ is chosen from a hydrogen atom, an —OH radical, —$NHR_{11}$ radicals and —$NR_{12}R_{13}$ radicals;

$R_{11}$ is chosen from a hydrogen atom, $C_1$–$C_4$ alkyl radicals, $C_1$–$C_4$ monohydroxyalkyl radicals, $C_2$–$C_4$ polyhydroxyalkyl radicals and a phenyl radical;

$R_{12}$ and $R_{13}$, which may be identical or different, are chosen from $C_1$–$C_4$ alkyl radicals, $C_1$–$C_4$ monohydroxyalkyl radicals and $C_2$–$C_4$ polyhydroxyalkyl radicals; or (b) a 5- or 6-membered nitrogenous heterocyclic group which can contain at least one other hetero atom and/or at least one carbonyl group and which can have at least one substituent chosen from $C_1$–$C_4$ alkyl, amino and phenyl radicals, and (ii) at least one compound chosen from glycerol, polyols containing at least 4 carbon atoms, $C_1$–$C_8$ aliphatic ethers of $C_3$–$C_9$ polyols, and $C_6$–$C_8$ aromatic ethers of $C_2$–$C_9$ polyols, and (iii) at least one oxidation base, and a second compartment contains a composition comprising at least one oxidizing agent.

34. A multi-compartment dyeing device or multi-compartment dyeing kit comprising at least two separate compartments wherein a first compartment contains a composition comprising:

(i) at least one cationic direct dye of formula (I) below:

A—N═N—B (I)

in which:

the symbol A represents a group chosen from structures $A_1$ to $A_3$ below:

$A_1$

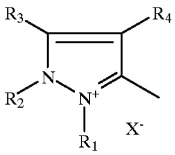

$A_2$

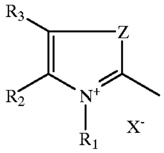

$A_3$

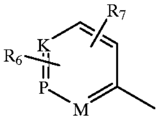

in which structures $A_1$ to $A_3$, $R_1$ is chosen from $C_1$–$C_4$ alkyl radicals and a phenyl radical having a substituent chosen from $C_1$–$C_4$ alkyl radicals and halogen atoms chosen from chlorine, bromine, iodine and fluorine;

$R_2$ is chosen from $C_1$–$C_4$ alkyl radicals and a phenyl radical;

$R_3$ and $R_4$, which may be identical or different, are chosen from $C_1$–$C_4$ alkyl radicals and a phenyl radical and, in the case of structure $A_1$, can together form a substituted benzene ring, and in the case of structure $A_2$, can together form a benzene ring optionally having at least one substituent chosen from $C_1$–$C_4$ alkyl, $C_1$–$C_4$ alkoxy and $NO_2$ radicals;

$R_3$ can also denote a hydrogen atom;

Z is chosen from an oxygen atom, a sulphur atom, and —$NR_2$ groups;

M is chosen from —CH, —CR, where R is chosen from $C_1$–$C_4$ alkyl radicals, and —$N^+R_5(X^-)_r$ groups;

K is chosen from —CH, —CR, where R is chosen from $C_1$–$C_4$ alkyl radicals, and —$N^+R_5(X^-)_r$ groups;

P is chosen from —CH, —CR, where R is chosen from $C_1$–$C_4$ alkyl radicals, and —$N^+R_5(X^-)_r$ groups;

r denotes 0 or 1;

$R_5$ is chosen from an atom $O^-$, $C_1$–$C_4$ alkoxy radicals and $C_1$–$C_4$ alkyl radicals;

$R_6$ and $R_7$, which may be identical or different, are chosen from a hydrogen atom, halogen atoms chosen from chlorine, bromine, iodine and fluorine, $C_1$–$C_4$ alkyl radicals, $C_1$–$C_4$ alkoxy radicals and an —$NO_2$ radical;

$X^-$ is an anion;

with the proviso that, if $R_4$ is a $C_1$–$C_4$ alkyl radical and Z is a sulphur atom, $R_3$ is not a hydrogen atom;

if $R_5$ is $O^-$, then r is zero;

if K or P or M is —$N^+$—$C_1$–$C_4$ -alkyl $X^-$, then $R_6$ or $R_7$ is other than a hydrogen atom;

if K is —$N^+R_5(X^-)_r$, then M═P and is —CH or —CR;

if M is —$N^+R_5(X^-)_r$, then K═P and is —CH or —CR;

if P is —$N^+R_5(X^-)_r$, then K═M and is —CH or —CR;

at least one of K, M, and P is —$N^+R_5(X^-)_r$;

if Z is —$NR_2$ and $R_2$ is a $C_1$–$C_4$ alkyl radical, then at least one of the radicals $R_1$, $R_3$ or $R_4$ of structure $A_2$ is other than a $C_1$–$C_4$ alkyl radical;

the symbol B represents:

(a) a group of structure $B_1$ below:

$B_1$

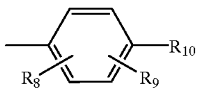

in which structure $B_1$, $R_8$ is chosen from a hydrogen atom, halogen atoms chosen from chlorine, bromine, iodine and fluorine, $C_1$–$C_4$ alkyl radicals, $C_1$–$C_4$ alkoxy radicals, a radical —OH, a radical —$NO_2$, —$NHR_{11}$ radicals, —$NR_{12}R_{13}$ radicals, and —$NHCO(C_1$–$C_4)$alkyl radicals or forms, with $R_9$, a 5- or 6-membered ring which may contain at least one hetero atom chosen from nitrogen, oxygen and sulphur;

$R_9$ is chosen from a hydrogen atom, halogen atoms chosen from chlorine, bromine, iodine and fluorine, $C_1$–$C_4$ alkyl radicals, and $C_1$–$C_4$ alkoxy radicals, or forms, with $R_{10}$ or $R_{11}$, a 5- or 6-membered ring which may contain at least one hetero atom chosen from nitrogen, oxygen and sulphur;

$R_{10}$ is chosen from a hydrogen atom, an —OH radical, —$NHR_{11}$ radicals and —$NR_{12}R_{13}$ $R_{11}$is chosen from a hydrogen atom, $C_1$–$C_4$ alkyl radicals, $C_1$–$C_4$ monohydroxyalkyl radicals, $C_2$–$C_4$ polyhydroxyalkyl radicals and a phenyl radical;

$R_{12}$ and $R_{13}$, which may be identical or different, are chosen from $C_1$–$C_4$ alkyl radicals, $C_1$–$C_4$ monohydroxyalkyl radicals and $C_2$–$C_4$ polyhydroxyalkyl radicals; or (b) a 5- or 6-membered nitrogenous heterocyclic group which can contain at least one other hetero atom and/or at least one carbonyl group and which can have at least one substituent chosen from $C_1$–$C_4$ alkyl, amino and phenyl radicals, and (ii) at least one compound chosen from glycerol, polyols containing at least 4 carbon atoms, $C_1$–$C_8$ aliphatic ethers of $C_3$–$C_9$ polyols, and $C_6$–$C_8$ aromatic ethers of $C_2$–$C_9$ polyols, and a second compartment contains a composition comprising at least one oxidizing agent.

35. A process for dyeing keratin fibers, comprising applying to said fibers, for a period which is sufficient to develop a desired coloration, at least one dye composition comprising:

(i) at least one cationic direct dye of formula (I) below:

(I)

A—N═N—B in which:

the symbol A represents a group chosen from structures $A_1$ to $A_3$ below:

$A_1$

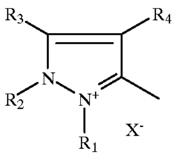

$A_2$

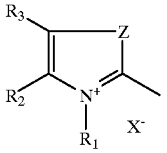

$A_3$

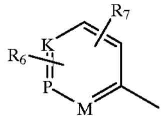

in which structures $A_1$ to $A_3$, $R_1$ is chosen from $C_1$–$C_4$ alkyl radicals and a phenyl radical having a substituent chosen from $C_1$–$C_4$ alkyl radicals and halogen atoms chosen from chlorine, bromine, iodine and fluorine;

$R_2$ is chosen from $C_1$–$C_4$ alkyl radicals and a phenyl radical; $R_3$ and $R_4$, which may be identical or different, are chosen from $C_1$–$C_4$ alkyl radicals and a phenyl radical and, in the case of structure $A_1$, can together form a substituted benzene ring, and in the case of structure $A_2$, can together form a benzene ring optionally having at least one substituent chosen from $C_1$–$C_4$ alkyl, $C_1$–$C_4$ alkoxy and $NO_2$ radicals;

$R_3$ can also denote a hydrogen atom;

Z is chosen from an oxygen atom, a sulphur atom, and —$NR_2$ groups;

M is chosen from —CH, —CR, where R is chosen from $C_1$–$C_4$ alkyl radicals, and —$N^+R_5(X^-)_r$ groups;

K is chosen from —CH, —CR, where R is chosen from $C_1$–$C_4$ alkyl radicals, and —$N^+R_5(X^-)_r$ groups;

P is chosen from —CH, —CR, where R is chosen from $C_1$–$C_4$ alkyl radicals, and —$N^+R_5(X^-)_r$ groups;

r denotes 0 or 1;

$R_5$ is chosen from an atom $O^-$, $C_1$–$C_4$ alkoxy radicals and $C_1$–$C_4$ alkyl radicals;

$R_6$ and $R_7$, which may be identical or different, are chosen from a hydrogen atom, halogen atoms chosen from chlorine, bromine, iodine and fluorine, $C_1$–$C_4$ alkyl radicals, $C_1$–$C_4$ alkoxy radicals and an —$NO_2$ radical;

$X^-$ is an anion;

with the proviso that, if $R_4$ is a $C_1$–$C_4$ alkyl radical and Z is a sulphur atom, $R_3$ is not a hydrogen atom;

if $R_5$ is $O^-$, then r is zero;

if K or P or M is —$N^+$—$C_1$–$C_4$ -alkyl $X^-$, then $R_6$ or $R_7$ is other than a hydrogen atom;

if K is —$N^+R_5(X^-)_r$, then M═P and is —CH or —CR;

if M is —$N^+R_5(X^-)_r$, then K═P and is —CH or —CR;

if P is —$N^+R_5(X^-)_r$, then K═M and is —CH or —CR;

at least one of K, M, and P is —$N^+R_5(X^-)_r$;

if Z is —$NR_2$ and $R_2$ is a $C_1$–$C_4$ alkyl radical, then at least one of the radicals $R_1$, $R_3$ or $R_4$ of structure $A_2$ is other than a $C_1$–$C_4$ alkyl radical;

the symbol B represents:

(a) a group of structure $B_1$ below:

$B_1$

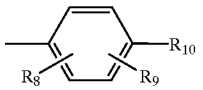

in which structure $B_1$, $R_8$ is chosen from a hydrogen atom, halogen atoms chosen from chlorine, bromine, iodine and fluorine, $C_1$–$C_4$ alkyl radicals, $C_1$–$C_4$ alkoxy radicals, a radical —OH, a radical —$NO_2$, —$NHR_{11}$ radicals, —$NR_{12}R_{13}$ radicals, and —$NHCO(C_1$–$C_4)$alkyl radicals or forms, with $R_9$, a 5- or 6-membered ring which may contain at least one hetero atom chosen from nitrogen, oxygen and sulphur;

$R_9$ is chosen from a hydrogen atom, halogen atoms chosen from chlorine, bromine, iodine and fluorine, $C_1$–$C_4$ alkyl radicals, and $C_1$–$C_4$ alkoxy radicals, or forms, with $R_{10}$ or $R_{11}$, a 5- or 6-membered ring which may contain at least one hetero atom chosen from nitrogen, oxygen and sulphur;

$R_{10}$ is chosen from a hydrogen atom, an —OH radical, —$NHR_{11}$ radicals and —$NR_{12}R_{13}$ radicals;

$R_{11}$ is chosen from a hydrogen atom, $C_1$–$C_4$ alkyl radicals, $C_1$–$C_4$ monohydroxyalkyl radicals, $C_2$–$C_4$ polyhydroxyalkyl radicals and a phenyl radical;

$R_{12}$ and $R_{13}$, which may be identical or different, are chosen from $C_1$–$C_4$ alkyl radicals, $C_1$–$C_4$ monohydroxyalkyl radicals and $C_2$–$C_4$ polyhydroxyalkyl radicals; or (b) a 5- or 6-membered nitrogenous heterocyclic group which can contain at least one other hetero atom and/or at least one carbonyl group and which can have at least one substituent chosen from $C_1$–$C_4$ alkyl, amino and phenyl radicals, and (ii) at least one compound chosen from glycerol, polyols containing at least 4 carbon atoms, $C_1$–$C_8$ aliphatic ethers of $C_3$–$C_9$ polyols, and $C_6$–$C_8$ aromatic ethers of $C_2$–$C_9$ polyols, and drying said fibers;

wherein said fibers are not rinsed or washed after applying said at least one dye composition before drying.

36. A composition for dyeing keratin fibers comprising:

(i) at least one cationic direct dye; and (ii) at least one compound chosen from glycerol, polyols containing at least 4 carbon atoms, $C_1$–$C_8$ aliphatic ethers of $C_3$–$C_9$ polyols, and $C_6$–$C_8$ aromatic ethers of $C_2$–$C_9$ polyols;

wherein said at least one cationic direct dye is chosen from structures $(I)_1$ to $(I)_{77}$ below:

$(I)_1$

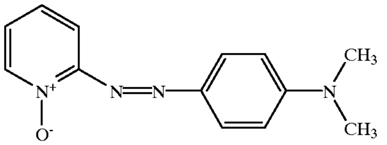

$(I)_2$

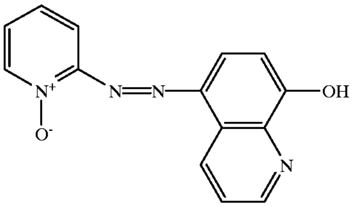

$(I)_3$

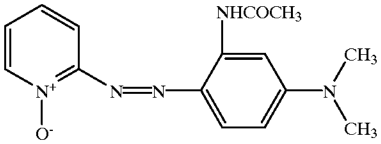

$(I)_4$

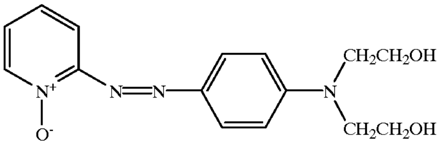

$(I)_5$

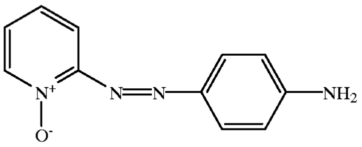

$(I)_6$

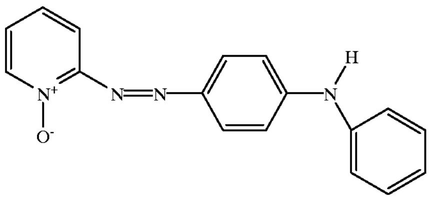

$(I)_7$

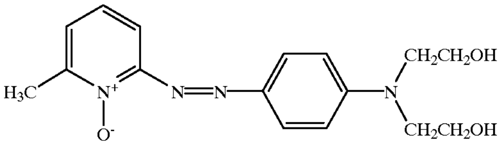

-continued $(I)_8$

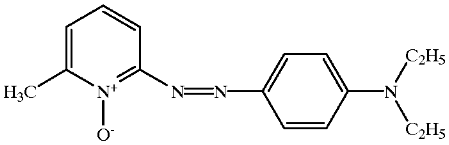

$(I)_9$

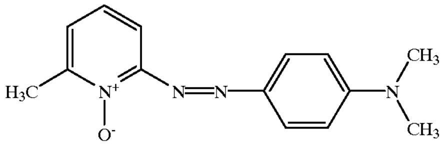

$(I)_{10}$

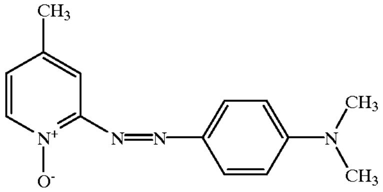

$(I)_{11}$

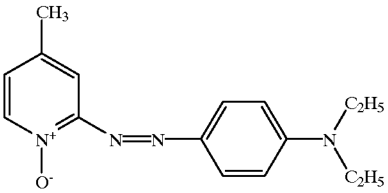

$(I)_{12}$

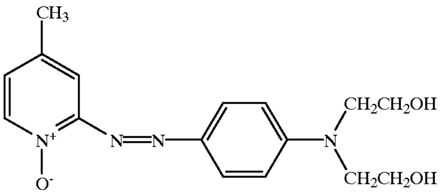

$(I)_{13}$

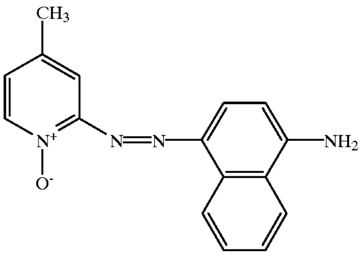

$(I)_{14}$

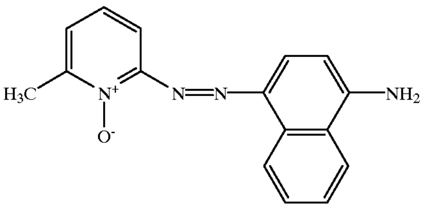

-continued
(I)15
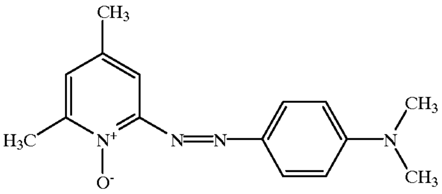
(I)16
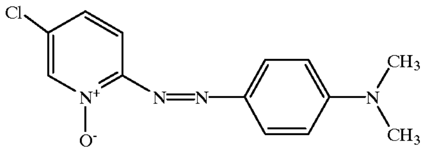
(I)17
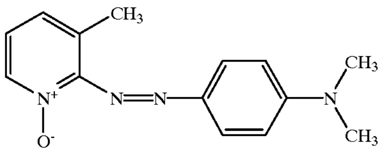
(I)18
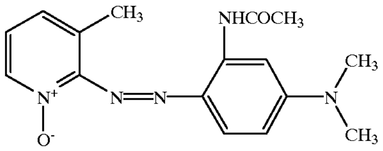
(I)19
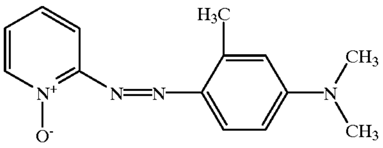
(I)20
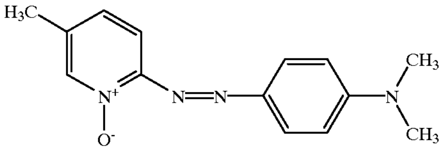
(I)21
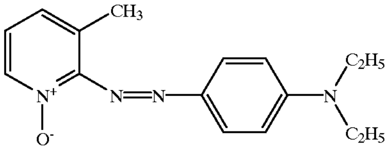
(I)22
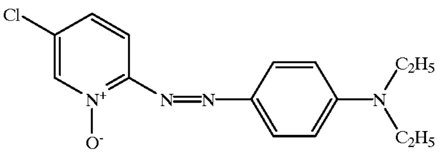
(I)23
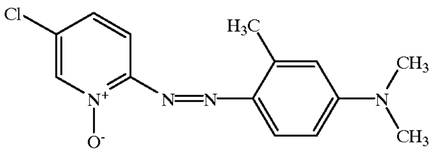
-continued
(I)24
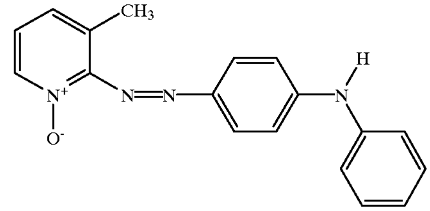
(I)25
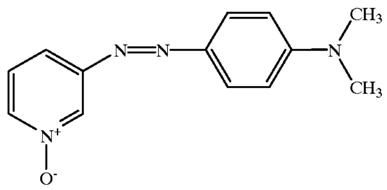
(I)26
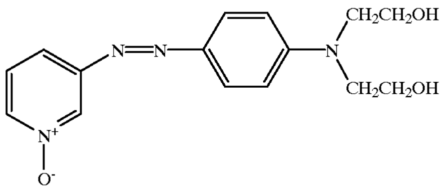
(I)27
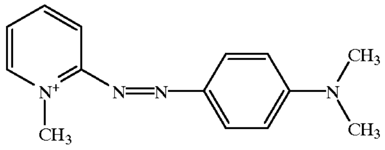
$CH_3SO_4^-$
(I)28
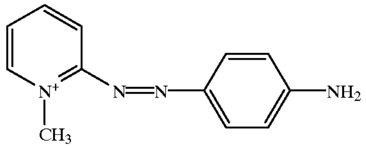
$CH_3SO_4^-$
(I)29
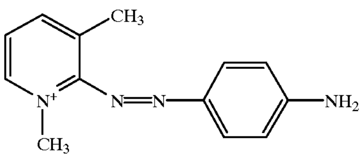
$CH_3SO_4^-$
(I)30
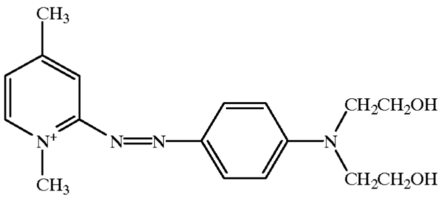
$CH_3SO_4^-$ -continued
(I)31
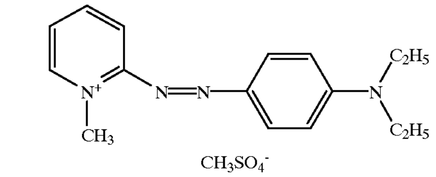
(I)32
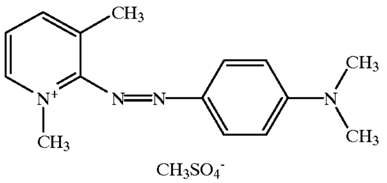
(I)33
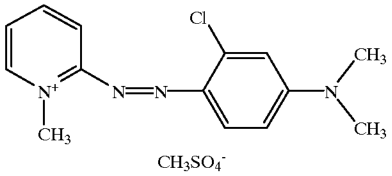
(I)34
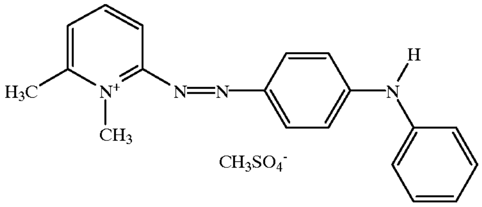
(I)35
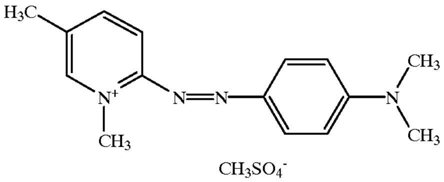
(I)36
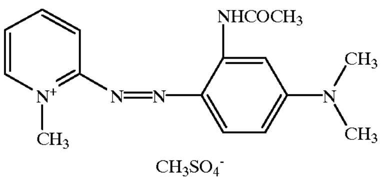
(I)37
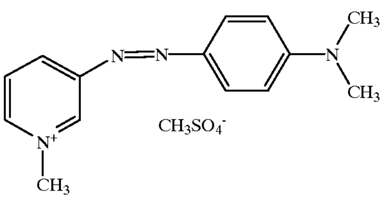
-continued
(I)38
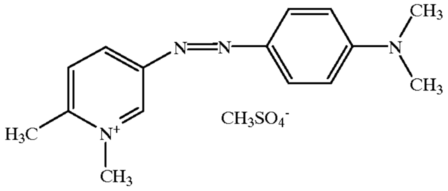
(I)39
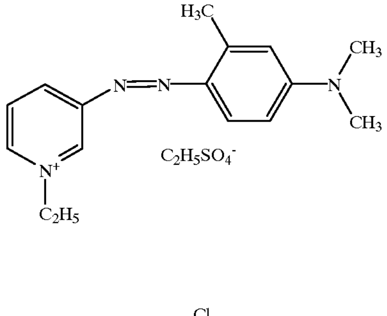
(I)40
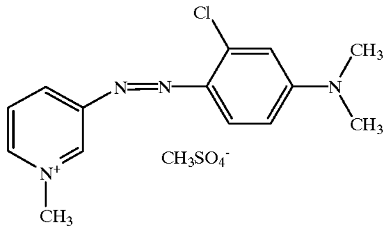
(I)41
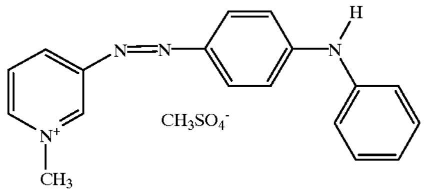
(I)42
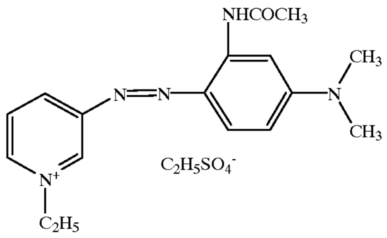
(I)43
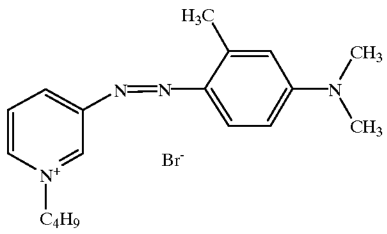

-continued
(I)44
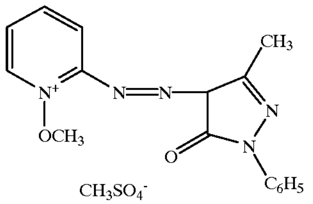
(I)45
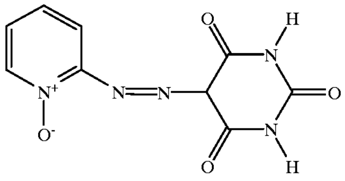
(I)46
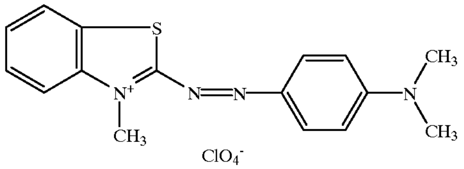
(I)47
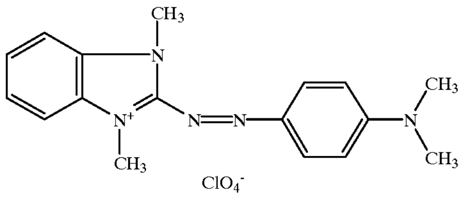
(I)48
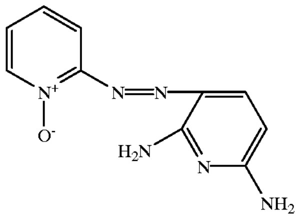
(I)49
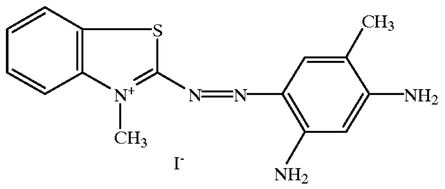
(I)50
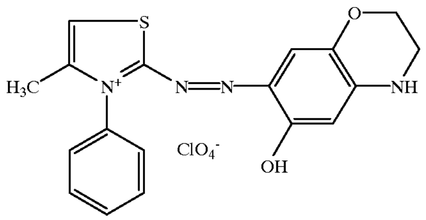
-continued
(I)51
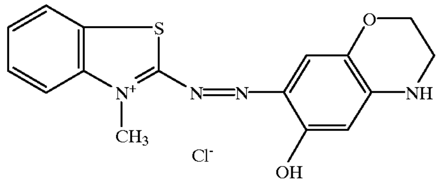
(I)52
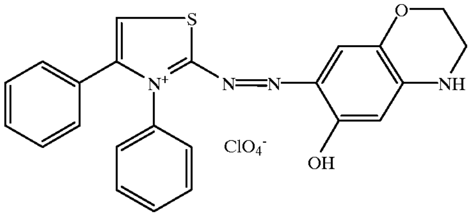
(I)53
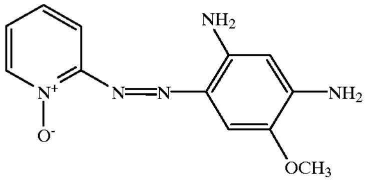
(I)54
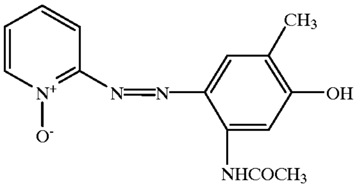
(I)55
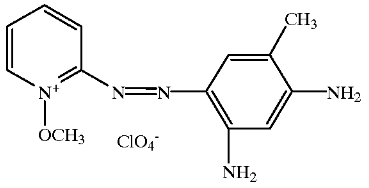
(I)56
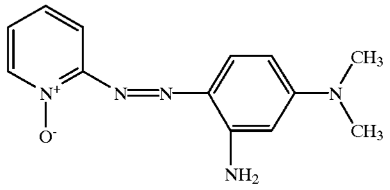
(I)57
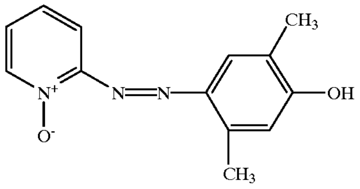

-continued
(I)$_{58}$
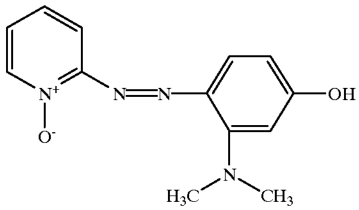
(I)$_{59}$
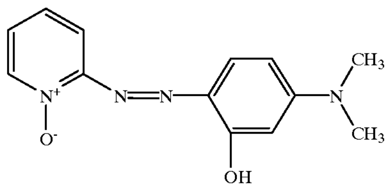
(I)$_{60}$
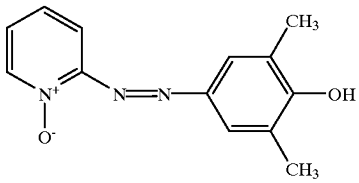
(I)$_{61}$
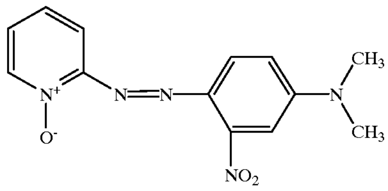
(I)$_{62}$
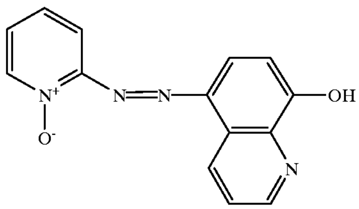
(I)$_{63}$
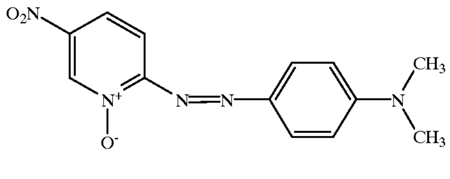
(I)$_{64}$
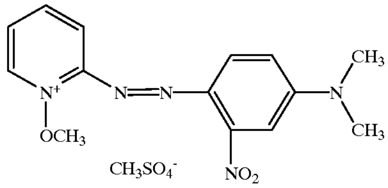
-continued
(I)$_{65}$
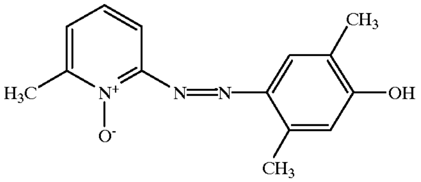
(I)$_{66}$
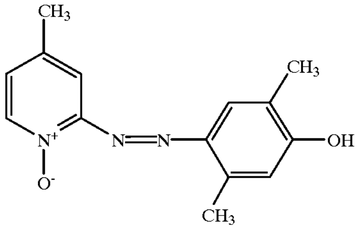
(I)$_{67}$
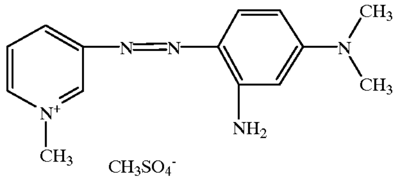
(I)$_{68}$
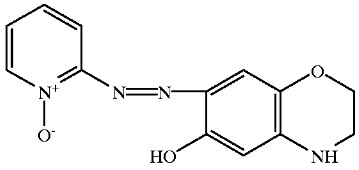
(I)$_{69}$
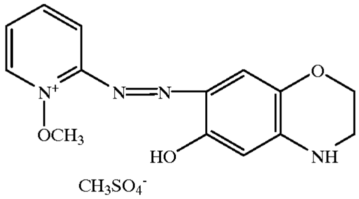
(I)$_{70}$
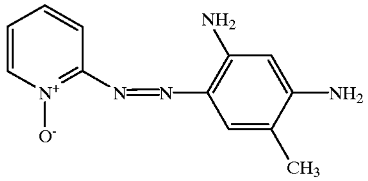
(I)$_{71}$
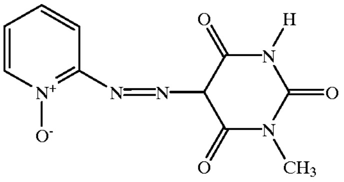

-continued
(I)72
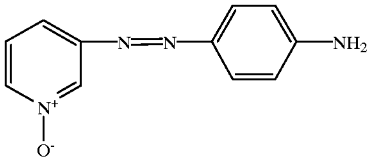
(I)73
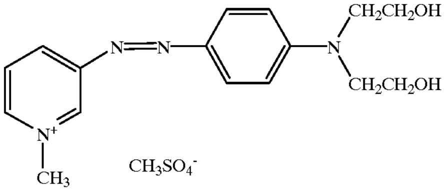
(I)74
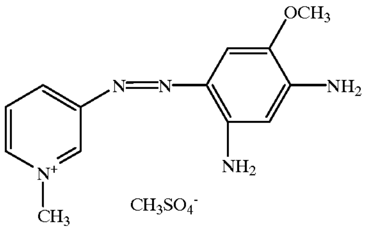
-continued
(I)75
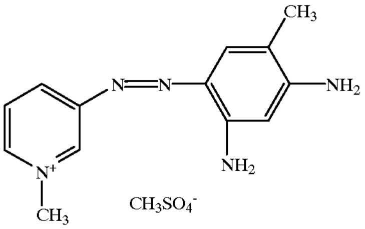
(I)76
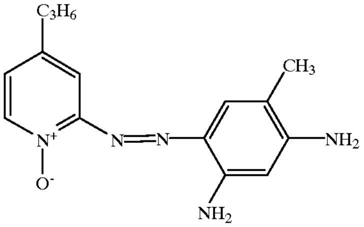
(I)77
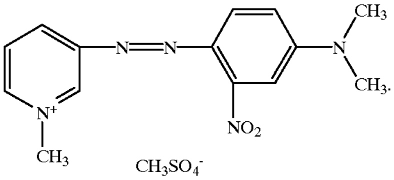
* * * * *

CERTIFICATE OF CORRECTION

PATENT NO. : 6,371,994 B2 
DATED : April 16, 2002
INVENTOR(S) : Lang et al.

It is certified that error appears in the above-identified patent and that said Letters Patent is hereby corrected as shown below:

Column 19,
Lines 2-8, structure $A_2$, “$R_2$” should read -- $R_4$ --.
Line 51, “$X^-$is” should read -- $X^-$ is --.

Column 21,
Line 1, move the structure located at the top of the column and insert said stucture after “a radical” on line 6.
Line 8, “$X^-$is” should read -- $X^-$ is --.
Line 44, “claim 1”, should read -- claim 12 --.
Line 51, “$C_3$-$C_9$polyols” should read -- $C_3$-$C_9$ polyols --.
Line 54, “herein” should read -- wherein --.

Column 22,
Line 11, “ah” should read -- an --.
Line 14, “claims” should read -- claim --.
Lines 53-59, structure $A_2$, “$R_2$” should read -- $R_4$ --.

Column 23,
Lines 1 and 5, “$C_1$-C4” should read -- $C_1$-$C_4$ --.
Line 47, “$(X^-)_t$” should read -- $(X^-)_r$ --.
Line 67, after “with”, delete the line break.

Column 24,
Lines 60-66, structure $A_2$, “$R_2$” should read -- $R_4$ --.

Column 25,
Line 50, “$X^-$is” should read -- $X^-$ is --.

Column 27,
Lines 9-15, structure $A_2$, “$R_2$” should read -- $R_4$ --.

Column 29,
Lines 18-24, structure $A_2$, “$R_2$” should read -- $R_4$ --.
Line 40, “$R_4$ which” should read -- $R_4$, which --.

Column 30,
Line 33, “-NHCO($C_1$-$C_4$) alkyl” should read -- -NHCO($C_1$-$C_4$)alkyl --.

UNITED STATES PATENT AND TRADEMARK OFFICE

CERTIFICATE OF CORRECTION

PATENT NO. : 6,371,994 B2
DATED : April 16, 2002
INVENTOR(S) : Lang et al.

It is certified that error appears in the above-identified patent and that said Letters Patent is hereby corrected as shown below:

Column 31,
Lines 21-27, structure $A_2$, "$R_2$" should read -- $R_4$ --.

Column 32,
Line 47, after "$-NR_{12}R_{13}$" insert -- radicals; --.
Line 48, "$R_{11}$is" should read -- $R_{11}$ is --.

Column 33,
Lines 22-28, structure $A_2$, "$R_2$" should read -- $R_4$ --.

Column 46,
Lines 13-20, structure $(I)_{76}$, "$C_3H_6$" should read -- $CH_3$ --.

Signed and Sealed this

Seventh Day of January, 2003

JAMES E. ROGAN
*Director of the United States Patent and Trademark Office*